(12) United States Patent
Davey et al.

(10) Patent No.: US 11,571,416 B2
(45) Date of Patent: Feb. 7, 2023

(54) AMODIAQUINE ANALOGS AND METHODS OF USES THEREOF

(71) Applicant: KAGOSHIMA UNIVERSITY, Kagoshima (JP)

(72) Inventors: Robert A. Davey, San Antonio, TX (US); Yasuteru Sakurai, San Antonio, TX (US); Masanori Baba, Kagoshima (JP); Norikazu Sakakibara, Kagoshima (JP)

(73) Assignee: Kagoshima University, Kagoshima (JP)

( * ) Notice: Subject to any disclaimer, the term of this patent is extended or adjusted under 35 U.S.C. 154(b) by 83 days.

(21) Appl. No.: 16/603,907

(22) PCT Filed: Apr. 13, 2018

(86) PCT No.: PCT/US2018/027528
§ 371 (c)(1),
(2) Date: Oct. 9, 2019

(87) PCT Pub. No.: WO2018/191642
PCT Pub. Date: Oct. 18, 2018

(65) Prior Publication Data
US 2020/0113891 A1    Apr. 16, 2020

Related U.S. Application Data

(60) Provisional application No. 62/485,273, filed on Apr. 13, 2017.

(51) Int. Cl.
| | |
|---|---|
| *A61K 31/4706* | (2006.01) |
| *A61P 31/14* | (2006.01) |
| *A61K 31/4709* | (2006.01) |
| *A61K 31/473* | (2006.01) |
| *A61K 31/496* | (2006.01) |
| *A61K 31/5377* | (2006.01) |
| *A61K 31/541* | (2006.01) |

(52) U.S. Cl.
CPC ........ *A61K 31/4706* (2013.01); *A61K 31/473* (2013.01); *A61K 31/4709* (2013.01); *A61K 31/496* (2013.01); *A61K 31/5377* (2013.01); *A61K 31/541* (2013.01); *A61P 31/14* (2018.01)

(58) Field of Classification Search
None
See application file for complete search history.

(56) References Cited

U.S. PATENT DOCUMENTS

| | | |
|---|---|---|
| 11,001,557 B2 | 5/2021 | Baba et al. |
| 2006/0142259 A1 | 6/2006 | Li |
| 2009/0226401 A1 | 9/2009 | Kim et al. |
| 2014/0011837 A1 | 1/2014 | Obi |
| 2019/0389803 A1 | 12/2019 | Baba et al. |

FOREIGN PATENT DOCUMENTS

| | | | |
|---|---|---|---|
| WO | 2013138200 | 9/2013 | |
| WO | WO-2018135449 A1 * | 7/2018 | ............ A61P 31/12 |

OTHER PUBLICATIONS

Zilbermintz et al. "Identification of Agents Effective Against Multiple Toxins and Viruses by Host-Oriented Cell Targeting". Scientific Reports. 2015; 5:13476. (Year: 2015).*
Sakurai et al. "Novel Amodiaquine Derivatives Potently Inhibit Ebola Virus Infection". Antiviral Research. Dec. 2018; 160:175-182. Published Online Nov. 3, 2018. (Year: 2018).*
Baba, Masanori, et al., Establishment of an antiviral assay system and identification of severe fever with thrombocytopenia syndrome virus inhibitors, Antivir. Chem. Chemother., 2017, vol. 25, No. 3, pp. 83-89.
Conroy A. E., et al., Heterocyclic Basic Componds. XII. 7-Bromo- and 7-Iodo-quinolines, J. Med. Chem. vol. 71, 1949, 3236-3237.
Wayhurst, D.C., et al., The chemotherapy of rodent malaria XXXIII, The activity of chloroquine and related blood schizontocides and some analogues in drug-induced pigment clumping, Ann. Trop. Med. Parasitol., vol. 76(3), 257-264, 1982.
Heindel, Ned. D., et al.. Synthesis and Antimalarial Activity of Amodiaquine Analogs, J. Med. Chem., 1970, vol. 13 (1), 156-157.
International Search Report and Written Opinion for PCT/US2018/027528, dated Jun. 29, 2018.
Zilbermintz et al., Identification of agents effective against multiple toxins and viruses by host-oriented cell targeting, Scientific Reports, Aug. 27, 2015.
Bertinaria et al., Amodiaquine analogues containing NO-donr substructures: Synthesis and their preliminary evaluation as potential tools in the treatment of cerebral malaria, European Journal of Medicinal Chemistry, Feb. 22, 2011.
Burckhalter et al., Aminoalkylphenois as Antimalarials. II. (Heterocyclic-amino)-a-amino-o-cresols. The Synthesis of Camoquin, Journal of the American Chemical Society, Apr. 1948.

* cited by examiner

*Primary Examiner* — Leslie A. Royds Draper
(74) *Attorney, Agent, or Firm* — Knobbe, Martens, Olson & Bear, LLP

(57) ABSTRACT

Described herein are pharmaceutical compositions capable of blocking entry of a virus into a host cell and containing one or more compounds of the general formula I or a pharmaceutically acceptable derivative thereof and methods of treatment or prophylactic administration of these pharmaceutical compositions to treat viral infections.

7 Claims, No Drawings

AMODIAQUINE ANALOGS AND METHODS OF USES THEREOF

CROSS-REFERENCE TO RELATED APPLICATIONS

This application claims the benefit of and priority to U.S. Provisional Application No. 62/485,273 filed on Apr. 13, 2017, which is incorporated herein by reference in its entirety.

FIELD

This disclosure relates to compositions containing analogs of amodiaquine and methods of use of these compositions to treat infections.

BACKGROUND

Ebolavirus causes a severe infectious disease with a high mortality rate ranging 25-90% in humans. The disease progresses rapidly and can be easily transmitted through direct contact with patients and contaminated materials. The December 2013-January 2016 outbreak in West Africa resulted in more than 28,000 infected cases with about 11,300 deaths. The virus spread to the neighboring areas, and also to USA and European countries due to the global movement of people, which was difficult to control. Thus, a significant public health threat arose all around the world. However, currently there is no approved treatment therapy for Ebolavirus infection. Although several antiviral candidates have been tested in patients, none have shown clear significant benefit and emphasizes a need for development of effective antiviral therapy.

SUMMARY

Disclosed herein are compounds and methods addressing the shortcomings of the art, and may provide any number of additional or alternative advantages. Described herein are compounds, compositions, and methods for ameliorating a symptom of an infection in an individual using specific amodiaquine derivatives. Certain embodiments include methods of treating Ebolavirus infections.

Disclosed here are pharmaceutical compositions capable of blocking entry of a virus into a host cell. These pharmaceutical compositions contain a compound of general formula I or a pharmaceutically acceptable derivative thereof, wherein R1 is a modified alkyl chain extending from a nitrogen, R2 is a halogen, R3 is a hydrogen or a phenol ring adduct; and R4 is a hydrogen or a phenyl group:

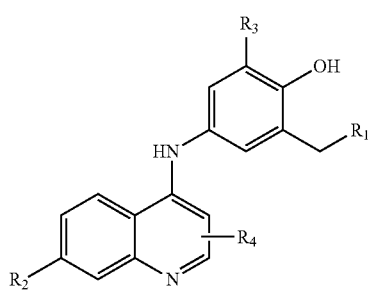

Formula I

In certain embodiments, R2 is bromine. In certain embodiments, R2 is chlorine. In certain embodiments, R2 is iodine. The pharmaceutical composition can include a therapeutically effective amount of a pharmaceutical composition containing a compound of general formula I, and a pharmaceutically acceptable carrier. Also provided herein are methods for treating or preventing a viral infection in a subject by administering to the subject a therapeutically effective amount of a pharmaceutical composition containing a compound of general formula I. The viral infection can be an Ebolavirus infection. In an embodiment, the pharmaceutical composition contains 4-(7-iodoquinolin-4-ylamino)-2-diethylaminomethylphenol. In an embodiment, the pharmaceutical composition contains 4-(7-chloroquinolin-4-ylamino)-2-dipropylamino methylphenol. In an embodiment, the pharmaceutical composition contains 4-(7-chloroquinolin-4-ylamino)-2-dibutylaminomethylphenol. In an embodiment, the pharmaceutical composition contains 4-(7-chloroquinolin-4-ylamino)-2-(ethylpropylamino)methylphenol. In an embodiment, the pharmaceutical composition contains 4-(7-chloroquinolin-4-ylamino)-2-(methylpropylamino) methylphenol. In an embodiment, the pharmaceutical composition contains 4-(7-iodoquinolin-4-ylamino)-2-methylpropylaminomethylphenol. In an embodiment, the pharmaceutical composition contains 4-(7-iodoquinolin-4-ylamino)-2-methylpentylaminomethylphenol. In an embodiment, the pharmaceutical composition contains 4-(7-iodoquinolin-4-ylamino)-2-hexylmethylaminomethylphenol. In an embodiment, the pharmaceutical composition contains 4-(7-iodoquinolin-4-ylamino)-2-methyloctylaminomethylphenol. In an embodiment, the pharmaceutical composition contains 4-(7-iodoquinolin-4-ylamino)-2-ethyl(2-hydroxyethyl) aminomethylphenol. In an embodiment, the pharmaceutical composition contains 4-(7-iodoquinolin-4-ylamino)-2-ethylpropylaminomethylphenol. In an embodiment, the pharmaceutical composition contains 4-(7-iodoquinolin-4-ylamino)-2-(1-piperidinylmethyl) phenol. In certain embodiments, the pharmaceutical composition can contain one or more of the compounds described herein that have a selectivity index greater than amiodiaquine. In certain embodiments, the pharmaceutical composition can contain one or more of the compounds described herein that have a selectivity index greater than 50. In certain embodiments, the pharmaceutical composition can contain one or more of the compounds described herein that have a selectivity index greater than 100. In certain embodiments, the pharmaceutical composition contain one or more of the compounds described herein that have a selectivity index greater than 200.

Also provided herein are methods for treating or preventing a pathogenic infection in a subject by administering to the subject a therapeutically effective amount of a pharmaceutical composition containing a compound of the general Formula I. The pathogenic infection can be a malarial infection, an Ebolavirus infection, or both.

Numerous other aspects, features and benefits of the present disclosure may be made apparent from the following detailed description taken together with the formulae and tables.

DETAILED DESCRIPTION

In the following description, numerous specific details are set forth in order to provide a thorough understanding of the various embodiments. In other instances, well-known processes and methods may not be described in particular detail in order not to unnecessarily obscure the embodiments described here. Additionally, illustrations of embodiments here may omit certain features or details in order to not obscure the embodiments described here.

In the following detailed description, reference is made to the accompanying formulae and tables that form a part of the specification. Other embodiments may be utilized, and logical changes may be made without departing from the scope of the disclosure. Therefore, the following detailed description is not to be taken in a limiting sense.

Patients with Ebolavirus disease, who were prescribed an anti-malaria drug, amodiaquine, had a significantly lower risk of death compared to other patients. Amodiaquine is a 4-aminoquinoline compound, which has been clinically used as an antimalarial drug for more than 60 years. It is on the World Health Organization's List of Essential Medicines and widely available in Africa at low cost. After rapid absorption in humans, amodiaquine undergoes rapid metabolism by cytochrome p450 2C8 (CYP2C8) enzyme to desethyl-amodiaquine, which has a long half-life of 9-18 days. Previous reports showed potent anti-Ebolavirus activity of both amodiaquine and the metabolite desetheyl-amodiaquine in cell culture. When malaria patients, who were also infected with Ebolavirus, were prescribed amodiaquine, these patients showed decreased case mortality compared to those getting another antimalarial drug or those taking no drugs. This suggests that amodiaquine may provide clinical benefit for Ebolavirus disease patients. However, the mortality rate only changed by from 65% to 50%. The need to improve the amodiaquine molecule was recognized, both by developing an optimal dosing formulation and regimen and also by finding more effective derivatives. Provided herein are amodiaquine derivatives of decreased toxicity and increased potency against Ebolavirus infection of cells.

In order to improve the antiviral activity of amodiaquine, a series of amodiaquine derivatives were developed and tested for their anti-Ebolavirus activity under BSL4 conditions. In an initial screening, fourteen compounds were more potent than amodiaquine against replication competent Ebolavirus. Several of them had selectivity indexes more than 130. The screening also revealed a defined structure-activity relationship. Hydrophobicity of the aminophenol-moiety at R1 and a halogen at R2 were key to increasing the antiviral activity without increasing cytotoxicity. Importantly, these features were independent of each other and were combined into one molecule. According to these structure-activity relationship analyses, a second set of derivatives was synthesized. All compounds in the second set contain iodine at R2 and a variety of alkyl chains at R1. Most of the derivatives efficiently blocked Ebola virus infection. Seven compounds yielded selectivity indexes more than 200 and appeared to have higher potential as anti-Ebola virus compounds than the potent compounds in the initial screening. For mechanistic analyses, pseudotype viruses and a minigenome system were used. The potent compounds worked by blocking host cell entry of Ebolavirus, and not by inhibiting genome replication. Taken together, this study found several amodiaquine-based compounds that potently inhibited Ebolavirus infection by targeting the entry step.

In an aspect, the disclosure provides a method of ameliorating a symptom of a viral disease in an individual, by administering an effective amount of a pharmaceutical composition containing a compound of general Formula I, or a pharmaceutically acceptable derivative thereof, to the individual, where the effective amount is an amount sufficient to ameliorate a symptom of the viral disease. In certain embodiments, the viral disease is Ebolavirus disease.

Embodiments include organic compounds satisfying formula I, or a pharmaceutically acceptable derivative thereof, wherein R1 is a modified alkyl chain extending from a nitrogen, R2 is a halogen, R3 is a hydrogen or a phenol ring adduct; and R4 is a hydrogen or a phenyl group. In certain embodiments, R2 is bromine. In certain embodiments, R2 is chlorine. In certain embodiments, R2 is iodine. The pharmaceutical composition can include a therapeutically effective amount of a pharmaceutical composition containing a compound of general formula I, and a pharmaceutically acceptable carrier. Also provided herein are methods for treating or preventing a viral infection in a subject by administering to the subject a therapeutically effective amount of a pharmaceutical composition having the general formula I. The viral infection can be an Ebolavirus infection. Also provided herein are methods for treating or preventing a pathogenic infection in a subject by administering to the subject a therapeutically effective amount of a pharmaceutical composition containing a compound of general formula I. The pathogenic infection can be a malarial infection, an Ebolavirus infection, or both.

Embodiments include organic compounds satisfying formula I, wherein R1 is a modified alkyl chain extended from a nitrogen, with a branch containing two or more carbon atoms or a closed carbon ring, which can contain hydroxyl groups, a nitrogen or an oxygen; R2 is a halogen; R3 is a hydrogen or a phenol ring adduct, and R4 is a hydrogen or a phenyl group. In certain embodiments, R2 is bromine. In certain embodiments, R2 is chlorine. In certain embodiments, R2 is iodine.

As used here, the following terms may have the following definitions. A "pharmaceutical composition" refers to a mixture of one or more of the compounds described herein, or a pharmaceutically acceptable derivative as an active ingredient, and at least one pharmaceutically acceptable carrier or excipient. The purpose of a pharmaceutical composition is to facilitate administration of a compound to a subject. In another aspect, a pharmaceutical composition can contain a compound of one of the formulae described herein, or a pharmaceutically acceptable derivative, and a pharmaceutically acceptable carrier or excipient. In some embodiments, the pharmaceutical composition includes two or more pharmaceutically acceptable carriers or excipients. In certain embodiments, the pharmaceutical composition can contain one or more of the compounds described herein that have a selectivity index greater than amiodiaquine. In certain embodiments, the pharmaceutical composition can contain one or more of the compounds described herein that have a selectivity index greater than 50. In certain embodiments, the pharmaceutical composition contains Compound 14: 4-(7-chloroquinolin-4-ylamino)-2-(methylpropylamino) methylphenol. In certain embodiments, the pharmaceutical composition contains Compound 29: 4-(7-chloroquinolin-4-ylamino)-2-(ethylpropylamino) methylphenol.

In certain embodiments, the pharmaceutical composition can contain one or more of the compounds described herein that have a selectivity index greater than 100. In certain embodiments, the pharmaceutical composition contains Compound 18: 4-(7-iodoquinolin-4-ylamino)-2-diethylaminomethylphenol. In certain embodiments, the pharmaceutical composition contains Compound 26: 4-(7-chloroquinolin-4-ylamino)-2-dipropylaminomethylphenol. In certain embodiments, the pharmaceutical composition contains Compound 28: 4-(7-chloroquinolin-4-ylamino)-2-dibutylaminomethylphenol. In certain embodiments, the pharmaceutical composition can contain Compound 30: 4-(7-iodoquinolin-4-ylamino)-2-dimethylaminomethylphenol. In certain embodiments, the pharmaceutical composition contains Compound 31: 4-(7-iodoquinolin-4-ylamino)-2-ethylmethylaminomethylphenol. In certain embodiments, the pharmaceutical composition contains Compound 32: 4-(7-iodoquinolin-4-ylamino)-2-isopropylmethylaminomethylphenol. In certain embodiments, the pharmaceutical composition can contain Compound 35: 4-(7-iodoquinolin-4-ylamino)-2-butylmethylaminomethylphenol. In certain embodiments, the pharmaceutical composition can contain Compound 41: 4-(7-iodoquinolin-4-ylamino)-2-ethylbutylaminomethylphenol.

In certain embodiments, the pharmaceutical composition can contain one or more of the compounds described herein that have a selectivity index greater than 200. In certain embodiments, the pharmaceutical composition can contain Compound 34: 4-(7-iodoquinolin-4-ylamino)-2-methylpropylaminomethylphenol. In certain embodiments, the pharmaceutical composition can contain Compound 36: 4-(7-iodoquinolin-4-ylamino)-2-methylpentylaminomethylphenol. In certain embodiments, the pharmaceutical composition can contain Compound 37: 4-(7-iodoquinolin-4-ylamino)-2-hexylmethylaminomethylphenol. In certain embodiments, the pharmaceutical composition can contain Compound 38: 4-(7-iodoquinolin-4-ylamino)-2-methyloctylaminomethylphenol. In certain embodiments, the pharmaceutical composition can contain Compound 39: 4-(7-iodoquinolin-4-ylamino)-2-ethyl(2-hydroxyethyl) aminomethylphenol. In certain embodiments, the pharmaceutical composition can contain Compound 40: 4-(7-iodoquinolin-4-ylamino)-2-ethylpropylaminomethylphenol. In certain embodiments, the pharmaceutical composition can contain Compound 43: 4-(7-iodoquinolin-4-ylamino)-2-(1-piperidinylmethyl)phenol.

The term "pharmaceutically acceptable derivative" as used herein refers to and includes any pharmaceutically acceptable salt, pro-drug, metabolite, ester, ether, hydrate, polymorph, solvate, complex, and adduct of a compound described herein which, upon administration to a subject, is capable of providing (directly or indirectly) the active ingredient. For example, the term "a pharmaceutically acceptable derivative" of compounds of general formula I includes all derivatives of the compounds of general formula I (such as salts, pro-drugs, metabolites, esters, ethers, hydrates, polymorphs, solvates, complexes, and adducts) which, upon administration to a subject, are capable of providing (directly or indirectly) the compounds of general formula I.

As used herein, the term "pharmaceutically acceptable salt" refers to those salts, which retain the biological effectiveness and properties of the parent compound. And unless otherwise indicated, a pharmaceutically acceptable salt includes salts of acidic or basic groups, which may be present in the compounds of the formulae disclosed herein. The present disclosure also provides certain processes, as examples, for the preparation of the above pharmaceutically acceptable salts, their derivatives, their analogs, their tautomeric forms, their stereoisomers, their polymorphs, and pharmaceutical compositions containing them.

Certain embodiments relate to pharmaceutically acceptable salts formed by the compounds of general formula I, their derivatives, their analogs, their tautomeric forms, their stereoisomers, their polymorphs and pharmaceutically acceptable compositions containing them. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenylsubstituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, beta-hydroxybutyrate, chloride, cinnamate, citrate, formate, fumarate, glycolate, heptanoate, lactate, maleate, hydroxymaleate, malonate, mesylate, nitrate, oxalate, phthalate, phosphate, monohydro genphosphate, dihydrogenphosphate, metaphosphate, pyrophosphate, propionate, phenylpropionate, salicylate, succinate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like.

Embodiments of the invention include pharmaceutical compositions including compounds of general formula I, or a pharmaceutically acceptable derivative, and a pharmaceutically acceptable carrier or excipient. Pharmaceutically acceptable ingredients, such as excipients, diluents, fillers, binders, and carriers can be inert or actively contribute to the delivery and distribution of the compounds of general formula I. The formulations used in embodiments herein include excipients, such as microcrystalline cellulose, lactose monohydrate, hydroxypropyl cellulose, croscarmellose sodium and magnesium stearate, preferably at least about 50 wt %, such as in the range from about 50% to about 95 wt %, including the range from about 50-90 wt %, and more preferably in the range from about 55-85 wt %, such as in the range from about 60% to about 85 wt %, or in the range from about 65 wt % to about 80 wt %, including about 60 wt %, about 65 wt %, about 70 wt %, about 75 wt %, or about 80 wt %.

An "effective amount" of a compound of general formula I is that amount sufficient to effect a desired biological effect, such as amelioration of symptoms and other clinical results, and, as such, an "effective amount" depends upon the context in which it is being applied. An effective amount of a compound of general formula I can be administered in one or more administrations.

Provided in Table 1 are the chemical structures and antiviral activities of amodiaquine and forty-five amodiaquine derivatives.

TABLE 1

| Compound # | R1 | R2 | R3 | R4 | IC50 (µM) |
|---|---|---|---|---|---|
| Amodiaquine | | Cl | H | H | 2.13 ± 0.32 |

TABLE 1-continued

| Compound # | R1 | R2 | R3 | R4 | IC50 (μM) |
|---|---|---|---|---|---|
| 1 | N(CH2C≡CH)2 | Cl | H | H | 5.78 ± 1.49 |
| 2 | N(Et)2 | CF3 | H | H | 5.87 ± 1.46 |
| 3 | N(Me)(Ph) | Cl | H | H | 6.39 ± 0.93 |
| 4 | N(Et)2 | Br | H | H | 1.55 ± 0.14 |
| 5 | N(Et)2 | F | H | H | 2.78 ± 0.28 |
| 6 | N(Et)2 | H | H | phenyl | 1.64 ± 0.22 |
| 7 | N(Et)2 | Cl | H | 3-methoxyphenyl | 0.73 ± 0.07 |
| 8 | N(Me)(iPr) | Cl | H | H | 1.46 ± 0.14 |
| 9 | NH(tBu) | Cl | H | H | 1.21 ± 0.09 |
| 10 | N(Me)2 | Cl | H | H | 2.14 ± 0.21 |
| 11 | N(Et)(iPr) | Cl | H | H | 1.46 ± 0.15 |
| 12 | N(Et)2 | H | H | H | 2.14 ± 0.18 |
| 13 | 4-methylpiperazin-1-yl | Cl | H | H | 1.68 ± 0.19 |

TABLE 1-continued

| Compound # | R1 | R2 | R3 | R4 | IC50 (μM) |
|---|---|---|---|---|---|
| 14 | N-methyl-N-propyl | Cl | H | H | 1.22 ± 0.11 |
| 15 | N-methyl-N-tert-butyl | Cl | H | H | 1.28 ± 0.07 |
| 16 | N,N-dimethyl-ethyl | Cl | H | H | 2.08 ± 0.22 |
| 17 | N-ethyl-N-(2-hydroxyethyl) | Cl | H | H | 1.77 ± 0.18 |
| 18 | N,N-diethyl | I | H | H | 0.64 ± 0.05 |
| 19 | 3-hydroxypiperidin-1-yl | Cl | H | H | 1.80 ± 0.28 |
| 20 | N,N-diethyl | Cl | 4-chlorophenyl | H | 1.31 ± 0.10 |
| 21 | pyrrolidin-1-yl | Cl | H | H | 1.09 ± n.d. |
| 22 | 3-hydroxypyrrolidin-1-yl | Cl | H | H | 1.73 ± 0.09 |
| 23 | N-pentyl | Cl | H | H | 0.29 ± 0.03 |
| 24 | morpholin-4-yl | Cl | H | H | 6.03 ± 0.41 |
| 25 | N-methyl-N-butyl | Cl | H | H | 0.86 ± 0.08 |
| 26 | N,N-dipropyl | Cl | H | H | 0.94 ± 0.08 |
| 27 | N,N-diallyl | Cl | H | H | 2.32 ± 0.32 |

TABLE 1-continued

| Compound # | R1 | R2 | R3 | R4 | IC50 (μM) |
|---|---|---|---|---|---|
| 28 | N(butyl)(butyl) | Cl | H | H | 0.72 ± 0.08 |
| 29 | N(ethyl)(propyl) | Cl | H | H | 1.39 ± 0.13 |
| 30 | N(methyl)(methyl) | I | H | H | 0.69 ± 0.08 |
| 31 | N(methyl)(ethyl) | I | H | H | 0.62 ± 0.06 |
| 32 | N(methyl)(isopropyl) | I | H | H | 0.29 ± 0.04 |
| 33 | N(methyl)(tert-butyl) | I | H | H | 0.30 ± 0.04 |
| 34 | N(methyl)(propyl) | I | H | H | 0.43 ± 0.06 |
| 35 | N(methyl)(butyl) | I | H | H | 0.44 ± 0.04 |
| 36 | N(methyl)(pentyl) | I | H | H | 0.37 ± 0.04 |
| 37 | N(propyl)(pentyl) | I | H | H | 0.39 ± 0.02 |
| 38 | N(pentyl)(pentyl) | I | H | H | 0.26 ± 0.06 |
| 39 | N(ethyl)(2-hydroxyethyl) | I | H | H | 0.41 ± 0.05 |
| 40 | N(ethyl)(propyl) | I | H | H | 0.36 ± 0.04 |
| 41 | N(ethyl)(butyl) | I | H | H | 0.41 ± 0.04 |
| 42 | pyrrolidin-1-yl | I | H | H | 0.66 ± 0.05 |

TABLE 1-continued

| Compound # | R1 | R2 | R3 | R4 | IC50 (µM) |
|---|---|---|---|---|---|
| 43 | piperidinyl | I | H | H | 0.37 ± 0.07 |
| 44 | morpholinyl | I | H | H | 1.59 ± 0.12 |
| 45 | thiomorpholinyl | I | H | H | 1.95 ± 0.22 |

Embodiments of the methods of synthesizing the amodiaquine derivatives are described by way of the following examples.

Example 1—Synthesis of Compound 1: 4-(7-chloroquinolin-4-ylamino)-2-bis(2-propyne-1-yl)aminomethylphenol Formula II The synthesis scheme for Compound 1 expressed as Formula II is shown in Reaction [I]. The term "reflux" refers to the process of increasing the rate of an organic reaction by supplying heat and using an appropriate condenser to return any evaporated reactant back to the reaction.

Reaction [I]

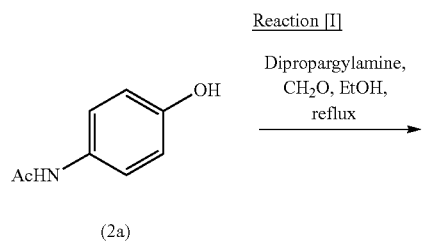

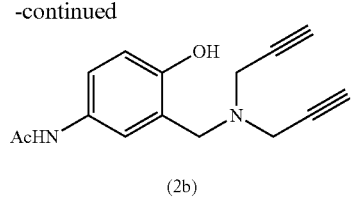

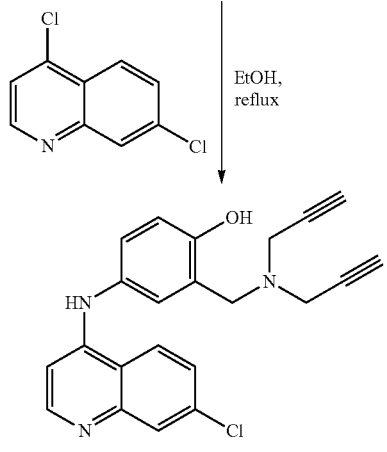

A mixture of 4-acetamidophenol (2a) (858.6 mg, 5.68 mmol) and 37% formaldehyde (848 µL, 8.52 mmol) was dissolved in ethanol (5 mL), and dipropargylamine (872 µL, 8.52 mmol) was added. The mixture was refluxed for approximately 12 h. The solvent was removed under reduced pressure, and the residue was purified by column chromatography using a mixture of ethyl acetate/methanol (5:1 v/v). N-3-bis(2-propyne-1-yl)aminomethyl-4-hydroxyphenyl)acetamide (2b) (433.9 mg, 1.69 mmol, 30% yield) was obtained as white crystals. Then, a mixture of N-3-bis(2-propyne-1-yl)aminomethyl-4-hydroxyphenylacetamide (2b) (128.2 mg, 0.50 mmol) and 4,7-dichloroquinoline (99 mg, 0.5 mmol) was dissolved in ethanol (5 mL), and the mixture was refluxed for approximately 6 h. The temperature of the reaction mixture was adjusted to 0° C. Then, 2% ammonia water (~5 mL) was added under stirring, and the precipitated crystals were separated using a Kiriyama funnel. The crude crystals were recrystallized from methanol, and Compound 1 (15 mg, 0.04 mmol, 8% yield) was obtained as a white powder. The resulting compound was analyzed by proton nuclear magnetic resonance (¹H NMR), carbon-13 nuclear magnetic resonance (¹³C NMR), and high-resolution mass spectrometry (HRMS) by electrospray ionization (ESI). The ¹H NMR data, ¹³C NMR data, the HRMS-ESI determination of mass, and melting point of Compound 1 are as follows.

The ¹H NMR data (400 MHz, CD$_3$OD): δ 8.32 (1H, d, J 5.6, quinoline-H), 8.27 (1H, d, J 8.8, quinoline-H), 7.84 (1H, d, J 2.0, quinoline-H), 7.48 (1H, dd, J 8.8 and 2.0, quinoline-H), 7.19 (1H, d, J 8.4, Ar—H), 7.17 (1H, s, Ar—H), 6.90 (1H, d, J 8.4, Ar—H), 6.67 (1H, d, J 5.6, quinoline-H), 3.91 (2H, s, ArCH$_2$N), 3.54 (4H, m, NCH$_2$CCH), 2.75 (2H, m, NCH$_2$CCH), and the ¹³C NMR data (100 MHz, CD$_3$OD): δ 156.3, 152.4, 150.1, 136.6, 132.4, 127.9, 127.7, 127.1, 126.4, 124.6, 124.5, 119.1, 117.7, 101.8, 78.6, 75.5, 55.0, 42.3, 30.7. The HRMS-ESI mass calculated for C$_{22}$H$_{19}$ClN$_3$O$^+$ [M+H]$^+$ was 376.12112; and the mass found was 376.12012. The melting point was determined to be about 189.0-189.4° C.

Example 2—Synthesis of Compound 2: 4-(2-trifluoromethylquinolin-4-ylamino)-2-diethylaminomethylphenol

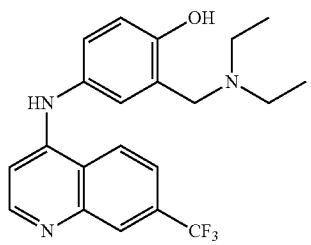

Formula III

Compound 2 (180.8 mg, 0.47 mmol, 93% yield) expressed as Formula III was obtained as a yellow oil using the same procedure as in Example 1, but with the use of 4-chloro-7-(trifluoromethyl)quinoline (115.8 mg, 0.50 mmol) instead of 4,7-dichloroquinoline (99.0 mg, 0.50 mmol). The resulting compound was analyzed by ¹H NMR, ¹³C NMR, and HRMS-ESI. The ¹H NMR data, ¹³C NMR data, the HRMS-ESI determination of mass, and melting point of Compound 2 are as follows.

The ¹H NMR data (400 MHz, CDCl$_3$): δ 8.57 (1H, d, J 5.2, quinoline-H), 8.31 (1H, s, quinoline-H), 8.00 (1H, d, J 8.8, quinoline-H), 7.65 (1H, dd, J 8.8 and 2.0, quinoline-H), 7.10 (1H, dd, J 8.4 and 2.4, Ar—H), 6.94 (1H, d, J 2.4, Ar—H), 6.88 (1H, d, J 8.4, Ar—H), 6.72 (1H, d, J 5.2, quinoline-H), 6.57 (1H, brs, Ar—OH), 3.79 (2H, s, ArCH$_2$N), 2.66 (4H, q, J 7.2, NCH$_2$CH$_3$), 1.15 (6H, t, J 7.2, NCH$_2$CH$_3$), and the ¹³C NMR data (100 MHz, CDCl$_3$): δ 156.9, 152.2, 149.2, 148.1, 131.3, 131.0, 129.7, 127.9 (d, J 4), 125.6, 125.4, 123.4, 120.8, 120.5 (d, J 3), 117.3, 102.4, 56.8, 46.5, 11.2. The HRMS-ESI mass calculated for C$_{21}$H$_{23}$F$_3$N$_3$O$^+$ [M+H]$^+$ was 390.17877; and the mass found was 390.17829. The melting point was determined to be about 189.9-190.6° C.

Example 3—Synthesis of Compound 3: 4-(7-chloroquinolin-4-yl-methylamino)-2-(methylphenylamino)methylphenol

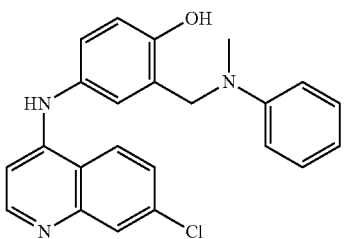

Formula IV

Compound 3 (42.0 mg, 0.11 mmol, 22% yield) expressed as Formula IV was obtained as a brown solid using the same procedure as in Example 1, but with the use of N-methylaniline (992 µL, 8.52 mmol) instead of dipropargylamine (872 µL, 8.52 mmol). The ¹H NMR data, ¹³C NMR data, the HRMS-ESI determination of mass, and melting point of Compound 3 are as follows.

The ¹H NMR data (400 MHz, CDCl$_3$): δ 8.41 (1H, d, J 5.2, quinoline-H), 8.00 (1H, d, J 2.0, quinoline-H), 7.83 (1H, d, J 8.8, quinoline-H), 7.39 (1H, dd, J 8.8 and 2.0, quinoline-H), 7.29 (2H, m, Ph-H), 7.07 (1H, dd, J 8.4 and 2.4, Ar—H), 7.02 (1H, m, Ar—H), 7.00 (3H, m, Ph-H), 6.93 (1H, d, J 8.4, Ar—H), 6.83 (1H, brs, Ar—NH—Ar), 6.60 (1H, d, J 5.2, quinoline-H), 4.45 (2H, s, ArCH$_2$N), 2.92 (3H, s, NCH$_3$), and the ¹³C NMR data (100 MHz, CDCl$_3$): δ 155.1, 151.4, 150.1, 149.6, 149.0, 135.4, 130.4, 129.3, 128.2, 125.9, 125.2, 125.0, 124.5, 121.3, 120.8, 117.4, 117.1, 117.0, 101.2, 57.1, 40.3. The HRMS-ESI mass calculated for C$_{23}$H$_{21}$ClN$_3$O$^+$ [M+H]$^+$ was 390.13677; and the mass found was 390.13602. The melting point was determined to be about 101.2-104.6° C.

Example 4—Synthesis of Compound 4: 4-(7-bromoquinolin-4-ylamino)-2-diethylamino-methylphenol

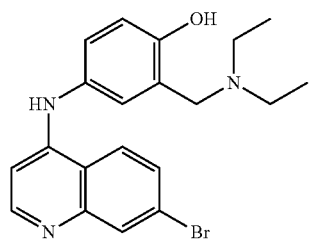

Formula V

Compound 4 (144.2 mg, 0.36 mmol, 72% yield) expressed as Formula V was obtained as a brown powder using the same procedure as in Example 1, but with the use of diethylamine (881 µL, 8.52 mmol) and 4-chloro-7-bromoquinoline (126.5 mg, 0.53 mmol) were used instead of dipropargylamine (872 µL, 8.52 mmol) and 4,7-dichloroquinoline (99.0 mg, 0.50 mmol), respectively. The ¹H NMR data, ¹³C NMR data, the HRMS-ESI determination of mass, and melting point of Compound 4 are as follows.

The ¹H NMR (400 MHz, CDCl$_3$): δ 8.45 (1H, d, J 5.2, quinoline-H), 8.18 (1H, d, J 2.4, quinoline-H), 7.75 (1H, d, J 8.8, quinoline-H), 7.56 (1H, dd, J 8.8 and 2.4, quinoline-H), 7.08 (1H, dd, J 8.4 and 2.4, Ar—H), 6.92 (1H, d, J 2.4, Ar—H), 6.86 (1H, d, J 8.4, Ar—H), 6.64 (1H, d, J 5.2, quinoline-H), 6.57 (1H, brs, Ar—OH), 3.79 (2H, s, ArCH$_2$N), 2.66 (4H, q, J 7.2, NCH$_2$CH$_3$), 1.14 (6H, t, J 7.2, NCH$_2$CH$_3$), and the $^{13}$C NMR data (100 MHz, CDCl$_3$): δ 156.7, 151.8, 149.6, 149.5, 132.1, 129.9, 128.3, 125.6, 125.3, 123.4, 121.0, 117.7, 117.1, 101.4, 56.8, 50.9, 46.4, 11.2. The HRMS-ESI mass calculated for C$_{20}$H$_{23}$BrN$_3$O$^+$ [M+H]$^+$ was 400.10190; and the mass found was 400.10155. The melting point was determined to be about 194.3-195.8° C.

Example 5—Synthesis of Compound 5: 4-(7-fluoroquinolin-4-ylamino)-2-diethylaminomethylphenol

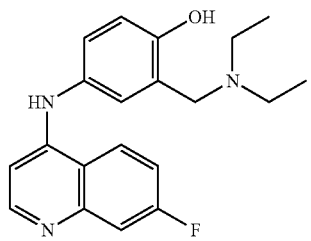

Formula VI

Compound 5 (108.5 mg, 0.32 mmol, 64% yield) expressed as Formula VI was obtained as a gray powder using the same procedure as in Example 1, but with the use of diethylamine (881 μL, 8.52 mmol) and 4-chloro-7-fluoroquinoline (95.3 mg, 0.53 mmol) were used instead of dipropargylamine (872 μL, 8.52 mmol) and 4,7-dichloroquinoline (99.0 mg, 0.50 mmol), respectively. The $^1$H NMR data, $^{13}$C NMR data, the HRMS-ESI determination of mass, and melting point of Compound 5 are as follows.

The $^1$H NMR (400 MHz, CDCl$_3$): δ 8.45 (1H, d, J 5.6, quinoline-H), 7.89 (1H, m, quinoline-H), 7.63 (1H, m, quinoline-H), 7.25 (1H, m, quinoline-H), 7.09 (1H, dd, J 8.4 and 2.4, Ar—H), 6.93 (1H, d, J 2.4, Ar—H), 6.86 (1H, d, J 8.4, Ar—H), 6.60 (1H, brs, Ar—OH), 6.59 (1H, d, J 5.6, quinoline-H), 3.78 (2H, s, ArCH$_2$), 2.65 (4H, q, J 7.2, NCH$_2$CH$_3$), 1.14 (6H, t, J 7.2, NCH$_2$CH$_3$), and the $^{13}$C NMR data (100 MHz, CDCl$_3$): δ 163.1 (d, J 248), 156.7, 151.9, 150.1 (d, J 12), 149.6, 129.9, 125.6, 125.3, 123.3, 121.7 (d, J 10), 117.2, 115.9, 115.0 (d, J 25), 113.4 (d, J 20), 100.8, 56.8, 50.8, 46.5, 11.2. The HRMS-ESI mass calculated for C$_{20}$H$_{23}$FN$_3$O$^+$ [M+H]$^+$ was 340.18197; and the mass found was 340.18174. The melting point was determined to be about 185.5-186.7° C.

Example 6—Synthesis of Compound 6: 4-(9-acridinylamino)-2-[(diethylamino)methyl]phenol

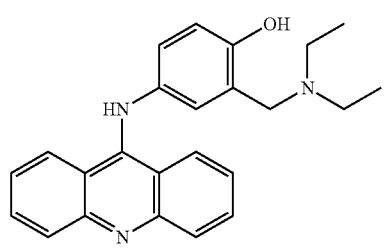

Formula VII

Compound 6 (90.0 mg, 0.25 mmol, 25% yield) expressed as Formula VII was obtained as a brown oil using the same procedure as in Example 1, but with the use of diethylamine (881 μL, 8.52 mmol) and 9-chloroacridine (213.6 mg, 1.00 mmol) instead of dipropargylamine (872 μL, 8.52 mmol) and 4,7-dichloroquinoline (99.0 mg, 0.50 mmol), respectively. The $^1$H NMR data, $^{13}$C NMR data, the HRMS-ESI determination of mass, and melting point of Compound 6 are as follows. The $^1$H NMR (400 MHz, CDCl$_3$): δ 7.97 (2H, d, J 8.8, acridine-H), 7.90 (2H, m, acridine-H), 7.97 (2H, m, acridine-H), 7.97 (2H, m, acridine-H), 6.88 (1H, dd, J 8.4 and 2.4, Ar—H), 6.77 (1H, d, J 8.4, Ar—H), 6.62 (1H, d, J 2.4, Ar—H), 3.64 (2H, s, ArCH$_2$N), 2.59 (4H, q, J 7.2, NCH$_2$CH$_3$), 1.09 (6H, t, J 7.2, NCH$_2$CH$_3$), and the $^{13}$C NMR data (100 MHz, CDCl$_3$): δ 154.5, 151.1, 138.1, 130.6, 123.2, 123.1, 120.4, 120.2, 118.4, 116.9, 116.5, 116.0, 115.7, 56.8, 46.3, 11.2. The HRMS-ESI mass calculated for C$_{24}$H$_{26}$N$_3$O$^+$ [M+H]$^+$ was 372.20704; and the mass found was 372.20636.

Example 7—Synthesis of Compound 7: 2-[(diethylamino)methyl]-4-[(2-chloro-6,7-dimethoxy-4-quinazolinyl)amino]phenol

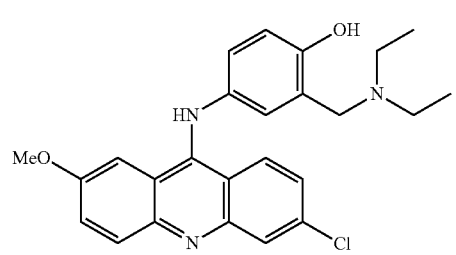

Formula VIII

Compound 7 (309.0 mg, 0.71 mmol, 71% yield) expressed as Formula VIII was obtained as a brown oil using the same procedure as in Example 1, but with the use of diethylamine (881 μL, 8.52 mmol) and 9-chloroacridine 2-methoxy-6,9-dichloroacridine (305.9 mg, 1.10 mmol) instead of dipropargylamine (872 μL, 8.52 mmol) and 4,7-dichloroquinoline (99.0 mg, 0.50 mmol), respectively. The $^1$H NMR data, $^{13}$C NMR data, the HRMS-ESI determination of mass, and melting point of Compound 7 are as follows.

The $^1$H NMR (400 MHz, CDCl$_3$): δ 8.03 (1H, s, acridine-H), 7.93 (1H, d, J 9.2, acridine-H), 7.82 (1H, d, J 9.2, acridine-H), 7.32 (1H, dd, J 9.2 and 2.4, acridine-H), 7.15 (1H, dd, J 9.2 and 1.6, acridine-H), 7.03 (1H, d, J 2.4, acridine-H), 6.81 (1H, dd, J 8.4 and 2.8, Ar—H), 6.73 (1H, d, J 8.4, Ar—H), 6.49 (1H, d, J 2.8, Ar—H), 3.65 (3H, s, OCH3), 3.60 (2H, s, ArCH$_2$N), 2.56 (4H, q, J 7.2, NCH$_2$CH$_3$), 1.06 (6H, t, J 7.2, NCH$_2$CH$_3$), and the $^{13}$C NMR data (100 MHz, CDCl$_3$): δ 155.9, 154.1, 147.8, 144.0, 136.3, 135.0, 127.2, 125.1, 125.0, 124.8, 123.0, 120.3, 120.0, 119.4, 117.4, 116.8, 56.8, 55.2, 46.3, 11.2. The HRMS-ESI mass calculated for C$_{25}$H$_{27}$ClN$_3$O$_2^+$ [M+H]$^+$ was 436.17863; and the mass found was 436.17705. The melting point was determined to be about 92.9-93.5° C.

Example 8—Synthesis of Compound 8: 4-(7-chloroquinolin-4-ylamino)-2-(isopropylmethylamino)methylphenol

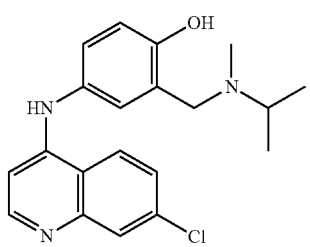

Formula IX

Compound 8 (42.0 mg, 0.11 mmol, 22% yield) expressed as Formula IX was obtained as a pale yellow solid using the same procedure as in Example 1, but with the use of methylisopropylaniline (878 µL, 8.52 mmol) instead of dipropargylamine (872 µL, 8.52 mmol). The $^1$H NMR data, $^{13}$C NMR data, the HRMS-ESI determination of mass, and melting point of Compound 8 are as follows.

The $^1$H NMR (400 MHz, CDCl$_3$): δ 8.46 (1H, d, J 5.6, quinoline-H), 7.99 (1H, d, J 2.0, quinoline-H), 7.85 (1H, d, J 8.8, quinoline-H), 7.41 (1H, dd, J 8.8 and 2.0, quinoline-H), 7.08 (1H, dd, J 8.4 and 2.4, Ar—H), 6.92 (1H, d, J 2.4, Ar—H), 6.85 (1H, d, J 8.4, Ar—H), 6.70 (1H, brs, Ar—OH), 6.62 (1H, d, J 5.6, quinoline-H), 3.77 (2H, s, ArCH$_2$N), 3.05 (1H, hept, J 6.8, NCH(CH$_3$)$_2$), 2.27 (6H, s, NCH$_3$), 1.12 (6H, d, J 6.8, NCH(CH$_3$)$_2$), and the $^{13}$C NMR data (100 MHz, CDCl$_3$): δ 156.9, 151.8, 149.4, 149.4, 135.2, 129.8, 128.8, 125.7, 125.6, 125.3, 123.1, 121.1, 117.4, 117.1, 101.3, 57.1, 52.8, 35.3, 17.3. The HRMS-ESI mass calculated for C$_{20}$H$_{23}$ClN$_3$O$^+$ [M+H]$^+$ was 356.15242; and the mass found was 356.15170. The melting point was determined to be about 98.2-99.8° C.

Example 9—Synthesis of Compound 9: 4-(7-chloroquinolin-4-ylamino)-2-tert-butylaminomethylphenol

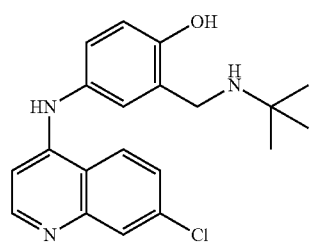

Formula X

Compound 9 (75.4 mg, 0.04 mmol, 4% yield) expressed as Formula X was obtained as a white solid using the same procedure as in Example 1, but with the use of tert-butylamine (902 µL, 8.52 mmol) instead of dipropargylamine (872 µL, 8.52 mmol). The 1H NMR data, 13C NMR data, the HRMS-ESI determination of mass, and melting point of Compound 9 are as follows.

The $^1$H NMR (400 MHz, CD$_3$OD): δ 8.33 (1H, d, J 5.6, quinoline-H), 8.31 (1H, d, J 8.8, quinoline-H), 7.86 (1H, d, J 2.0, quinoline-H), 7.52 (1H, dd, J 8.8 and 2.0, quinoline-H), 7.40 (1H, d, J 2.4, Ar—H), 7.30 (1H, dd, J 8.4 and 2.4, Ar—H), 7.03 (1H, d, J 8.4, Ar—H), 6.69 (1H, d, J 5.6, quinoline-H), 4.20 (2H, s, ArCH$_2$N), 1.48 (9H, s, NC(CH$_3$)$_3$), and the $^{13}$C NMR data (100 MHz, CD$_3$OD): δ 156.0, 152.5, 152.0, 149.7, 137.0, 132.5, 129.4, 129.2, 127.4, 126.7, 124.7, 121.0, 119.0, 117.5, 101.9, 58.3, 42.5, 26.0. The HRMS-ESI mass calculated for C$_{20}$H$_{23}$ClN$_3$O$^+$ [M+H]$^+$ was 356.15242; and the mass found was 356.15179. The melting point was determined to be about 237.8-238.4° C.

Example 10—Synthesis of Compound 10: 4-(7-chloroquinolin-4-ylamino)-2-dimethylaminomethylphenol

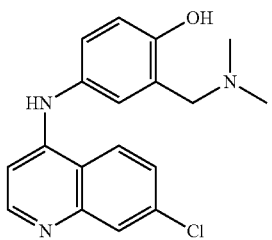

Formula XI

Compound 10 (142.9 mg, 0.44 mmol, 39% yield) expressed as Formula XI was obtained as a white solid using the same procedure as in Example 1, but with the use of dimethylamine (695 µL, 8.52 mmol) instead of dipropargylamine (872 µL, 8.52 mmol). The 1H NMR data, 13C NMR data, the HRMS-ESI determination of mass, and melting point of Compound 10 are as follows.

The $^1$H NMR (400 MHz, CDCl$_3$): δ 8.48 (1H, d, J 5.2, quinoline-H), 8.00 (1H, d, J 2.4, quinoline-H), 7.82 (1H, d, J 8.8, quinoline-H), 7.42 (1H, dd, J 8.8 and 2.4, quinoline-H), 7.10 (1H, dd, J 8.4 and 2.4, Ar—H), 6.92 (1H, d, J 2.4, Ar—H), 6.89 (1H, d, J 8.4, Ar—H), 6.62 (1H, d, J 5.2, quinoline-H), 6.52 (1H, brs, Ar—OH), 3.66 (2H, s, ArCH$_2$N), 2.37 (6H, s, NCH$_3$), and the $^{13}$C NMR data (100 MHz, CDCl$_3$): δ 156.5, 152.0, 149.6, 149.2, 135.1, 130.0, 129.0, 125.8, 125.2, 123.1, 120.9, 117.4, 117.2, 101.4, 76.7, 62.7, 44.5. The HRMS-ESI mass calculated for C$_{18}$H$_{19}$ClN$_3$O$^+$ [M+H]$^+$ was 328.12112; and the mass found was 328.12068. The melting point was determined to be about 210.9-212.1° C.

Example 11—Synthesis of Compound 11: 4-(7-chloroquinolin-4-ylamino)-2-(ethylisopropylamino)methylphenol

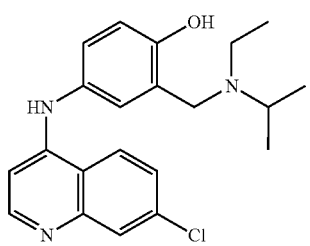

Formula XII

Compound 11 (302.9 mg, 0.30 mmol, 30% yield) expressed as Formula XII was obtained as a brown solid using the same procedure as in Example 1, but with the use of ethylisopropylamine (1031 μL, 8.52 mmol) of dipropargylamine (872 μL, 8.52 mmol). The $^1$H NMR data, $^{13}$C NMR data, the HRMS-ESI determination of mass, and melting point of Compound 11 are as follows.

The $^1$H NMR (400 MHz, CDCl$_3$): δ 8.48 (1H, d, J 5.6, quinoline-H), 7.99 (1H, d, J 1.6, quinoline-H), 7.82 (1H, d, J 8.8, quinoline-H), 7.42 (1H, dd, J 8.8 and 1.6, quinoline-H), 7.07 (1H, dd, J 8.4 and 2.0, Ar—H), 6.92 (1H, d, J 2.0, Ar—H), 6.84 (1H, d, J 8.4, Ar—H), 6.63 (1H, d, J 5.6, quinoline-H), 6.54 (1H, brs, Ar—OH), 3.80 (2H, s, ArCH$_2$N), 3.15 (1H, hept, J 6.8, NCH(CH$_3$)$_2$), 2.58 (2H, q, J 7.2, NCH$_2$CH$_3$), 1.17 (3H, t, J 7.2, NCH$_2$CH$_3$), 1.11 (6H, d, J 6.8, NCH(CH$_3$)$_2$), and the $^{13}$C NMR data (100 MHz, CDCl$_3$): δ 156.9, 152.0, 149.6, 149.3, 135.1, 129.8, 129.0, 125.7, 125.4, 125.3, 123.5, 121.0, 117.4, 117.2, 101.4, 52.8, 49.4, 43.1, 17.3, 13.3. The HRMS-ESI mass calculated for C$_{21}$H$_{25}$ClN$_3$O$^+$ [M+H]$^+$ was 370.16807; and the mass found was 370.16749. The melting point was determined to be about 174.8-175.8° C.

Example 12—Synthesis of Compound 12: 2-[(diethylamino)methyl]-4-(quinolin-4-ylamino)phenol

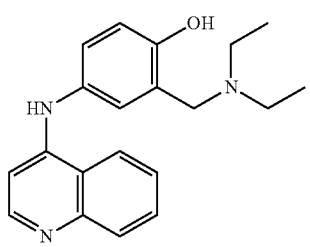

Formula XIII

Compound 12 (108.5 mg, 0.32 mmol, 64% yield) expressed as Formula XIII was obtained as a gray powder using the same procedure as in Example 1, but with the use of diethylamine (881 μL, 8.52 mmol) and 4-chloroquinoline (81.8 mg, 0.50 mmol) instead of dipropargylamine (872 μL, 8.52 mmol) and 4,7-dichloroquinoline (99.0 mg, 0.50 mmol), respectively. The 1H NMR data, 13C NMR data, the HRMS-ESI determination of mass, and melting point of Compound 12 are as follows.

The $^1$H NMR (400 MHz, CDCl$_3$): δ 8.50 (1H, d, J 5.2, quinoline-H), 8.02 (1H, d, J 8.4, quinoline-H), 7.88 (1H, d, J 8.4, quinoline-H), 7.68 (1H, m, quinoline-H), 7.49 (1H, m, quinoline-H), 7.10 (1H, dd, J 8.8 and 2.4, Ar—H), 6.94 (1H, d, J 2.4, Ar—H), 6.86 (1H, d, J 8.8, Ar—H), 6.52 (1H, brs, Ar—OH), 3.79 (2H, s, ArCH$_2$N), 2.66 (4H, q, J 7.2, NCH$_2$CH$_3$), 1.14 (6H, t, J 7.2, NCH$_2$CH$_3$), and the $^{13}$C NMR data (100 MHz, CDCl$_3$): δ 156.5, 151.0, 149.1, 148.9, 130.3, 130.2, 129.2, 125.4, 125.2, 125.0, 123.3, 119.3, 119.0, 117.1, 101.1, 56.9, 46.4, 11.2. The HRMS-ESI mass calculated for C$_{20}$H$_{24}$N$_3$O+[M+H]$^+$ was 322.19139; and the mass found was 322.19072. The melting point was determined to be about 156.3-156.9° C.

Example 13—Synthesis of Compound 13: 4-(7-chloroquinolin-4-ylamino)-2-(4-methyl-1-piperazinyl)methylphenol

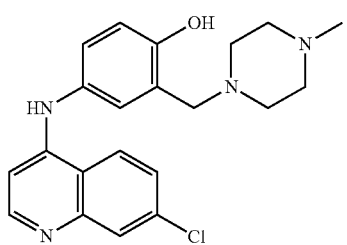

Formula XIV

Compound 13 (377.3 mg, 1.08 mmol, 36% yield) expressed as Formula XIV was obtained as yellow needle crystal using the same procedure as in Example 1, but with the use of 4-methylpiperazine (948 μL, 8.52 mmol) instead of dipropargylamine (872 μL, 8.52 mmol). The $^1$H NMR data, $^{13}$C NMR data, the HRMS-ESI determination of mass, and melting point of Compound 13 are as follows.

The $^1$H NMR (400 MHz, CDCl$_3$): δ 8.47 (1H, d, J 5.2, quinoline-H), 8.00 (1H, d, J 2.0, quinoline-H), 7.83 (1H, d, J 8.8, quinoline-H), 7.42 (1H, dd, J 8.8 and 2.0, quinoline-H), 7.12 (1H, dd, J 8.4 and 2.4, Ar—H), 6.95 (1H, d, J 2.4, Ar—H), 6.89 (1H, d, J 8.4, Ar—H), 6.62 (1H, d, J 5.2, quinoline-H), 6.60 (1H, brs, Ar—OH), 3.73 (2H, s, ArCH$_2$N), 2.59 (8H, m, piperazinyl-H), 2.33 (4H, m, piperazinyl-CH$_3$), and the $^{13}$C NMR data (100 MHz, CDCl$_3$): δ 156.1, 151.8, 149.4, 149.3, 135.3, 130.2, 128.8, 125.8, 125.8, 125.5, 122.4, 121.0, 117.4, 117.2, 101.3, 61.2, 54.9, 52.5, 45.9. The HRMS-ESI mass calculated for C$_{21}$H$_{24}$ClN$_4$O$^+$ [M+H]$^+$ was 383.16332; and the mass found was 383.16242. The melting point was determined to be about 173.3-174.1° C.

Example 14—Synthesis of Compound 14: 4-(7-chloroquinolin-4-ylamino)-2-(methylpropylamino)methylphenol

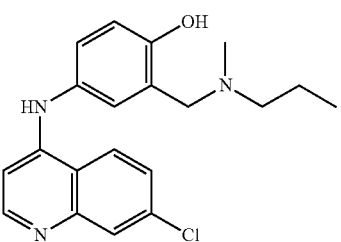

Formula XV

Compound 14 (602.6 mg, 1.69 mmol, 48% yield) expressed as Formula XV was obtained as a pale yellow solid using the same procedure as in Example 1, but with the use of N-methylpropylamine (874 μL, 8.52 mmol) instead of dipropargylamine (872 μL, 8.52 mmol). The $^1$H NMR data, $^{13}$C NMR data, the HRMS-ESI determination of mass, and melting point of Compound 14 are as follows.

The $^1$H NMR (400 MHz, CDCl$_3$): δ 8.47 (1H, d, J 5.2, quinoline-H), 7.99 (1H, d, J 2.0, quinoline-H), 7.82 (1H, d, J 8.8, quinoline-H), 7.41 (1H, dd, J 8.8 and 2.0, quinoline- H), 7.09 (1H, dd, J 8.4 and 2.0, Ar—H), 6.92 (1H, d, J 2.0, Ar—H), 6.87 (1H, d, J 8.4, Ar—H), 6.62 (1H, d, J 5.2, quinoline-H), 6.60 (1H, brs, Ar—OH), 3.70 (2H, s, ArCH$_2$N), 2.47 (2H, m, NCH$_2$CH$_2$CH$_3$), 2.31 (3H, s, NCH$_3$), 1.60 (2H, m, NCH$_2$CH$_2$CH$_3$), 0.95 (3H, t, J 7.2, NCH$_2$CH$_2$CH$_3$), and the $^{13}$C NMR data (100 MHz, CDCl$_3$): δ 156.5, 152.0, 149.6, 149.3, 135.1, 129.9, 129.0, 125.7, 125.6, 125.3, 123.2, 121.0, 117.4, 117.1, 101.4, 61.3, 59.0, 41.1, 20.1, 11.6. The HRMS-ESI mass calculated for C$_{20}$H$_{23}$ClN$_3$O$^+$ [M+H]$^+$ was 356.15242; and the mass found was 356.15188. The melting point was determined to be about 174.5-175.3° C.

Example 15—Synthesis of Compound 15: 4-(7-chloroquinolin-4-ylamino)-2-(tert-butylmethyl-amino)methylphenol

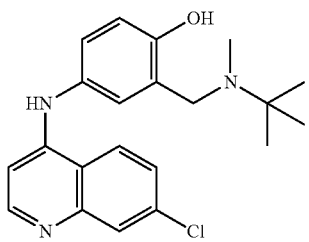

Formula XVI

Compound 15 (113.0 mg, 0.31 mmol, 9% yield) expressed as Formula XVI was obtained as a pale yellow solid using the same procedure as in Example 1, but with the use of N-tert-butylmethylamine (1021 μL, 8.52 mmol) instead of dipropargylamine (872 μL, 8.52 mmol). The $^1$H NMR data, $^{13}$C NMR data, the HRMS-ESI determination of mass, and melting point of Compound 15 are as follows.

The $^1$H NMR (400 MHz, CDCl$_3$): δ 8.48 (1H, d, J 5.6, quinoline-H), 8.00 (1H, d, J 2.0, quinoline-H), 7.81 (1H, d, J 8.8, quinoline-H), 7.43 (1H, dd, J 8.8 and 2.0, quinoline-H), 7.07 (1H, dd, J 8.4 and 2.4, Ar—H), 6.91 (1H, d, J 2.4, Ar—H), 6.84 (1H, d, J 8.4, Ar—H), 6.62 (1H, d, J 5.6, quinoline-H), 6.45 (1H, brs, Ar—OH), 3.85 (2H, brs, ArCH$_2$N), 2.30 (3H, s, NCH$_3$), 1.24 (9H, s, NC(CH$_3$)$_3$), and the $^{13}$C NMR data (100 MHz, CDCl$_3$): δ 156.9, 152.0, 149.6, 149.2, 135.1, 129.7, 129.1, 125.7, 125.4, 125.3, 123.5, 120.9, 117.4, 117.2, 101.4, 55.0, 54.4, 34.6, 25.8. The HRMS-ESI mass calculated for C$_{21}$H$_{25}$ClN$_3$O$^+$ [M+H]$^+$ was 370.16807; and the mass found was 370.16768. The melting point was determined to be about 185.4-187.8° C.

Example 16—Synthesis of Compound 16: 4-(7-chloroquinolin-4-ylamino)-2-(ethylmethylamino) methylphenol

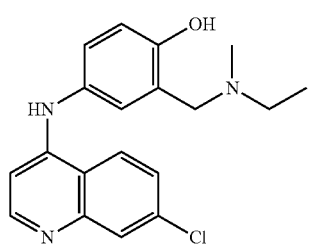

Formula XVII

Compound 16 (829.8 mg, 2.43 mmol, 61% yield) expressed as Formula XVII was obtained as a white solid using the same procedure as in Example 1, but with the use of N-ethylmethylamine (730 μL, 8.52 mmol) instead of dipropargylamine (872 μL, 8.52 mmol). The 1H NMR data, 13C NMR data, the HRMS-ESI determination of mass, and melting point of Compound 16 are as follows.

The $^1$H NMR (400 MHz, CD$_3$OD): δ 8.30 (1H, d, J 5.6, quinoline-H), 8.25 (1H, d, J 8.8, quinoline-H), 7.83 (1H, d, J 2.0, quinoline-H), 7.47 (1H, dd, J 8.8 and 2.0, quinoline-H), 7.14 (1H, dd, J 8.4 and 2.4, Ar—H), 7.06 (1H, d, J 2.4, Ar—H), 6.84 (1H, d, J 8.4, Ar—H), 6.63 (1H, d, J 5.6, quinoline-H), 3.75 (2H, s, ArCH$_2$N), 2.61 (2H, q, J 7.2, NCH$_2$CH$_3$), 2.35 (3H, s, NCH$_3$), 1.18 (3H, t, J 7.2, NCH$_2$CH$_3$), and the $^{13}$C NMR data (100 MHz, CD$_3$OD): δ 157.3, 152.5, 152.4, 150.1, 136.6, 131.9, 127.7, 127.2, 126.8, 126.4, 124.8, 124.5, 119.1, 117.7, 101.7, 60.6, 51.7, 41.1, 12.3. The HRMS-ESI mass calculated for C$_{19}$H$_{21}$ClN$_3$O$^+$ [M+H]$^+$ was 342.13677; and the mass found was 342.13629. The melting point was determined to be about 182.9-184.4° C.

Example 17—Synthesis of Compound 17: 4-(7-chloroquinolin-4-ylamino)-2-[ethyl(2-hydroxyethyl) amino]methylphenol

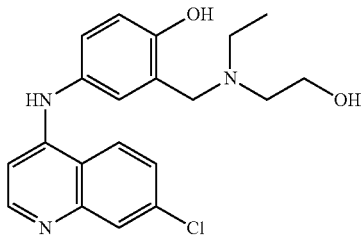

Formula XVIII

Compound 17 (612.1 mg, 1.63 mmol, 40% yield) expressed as Formula XVIII was obtained as a pale yellow solid using the same procedure as in Example 1, but with the use of ethyl(2-hydroxyethyl)amine (826 μL, 8.52 mmol) instead of dipropargylamine (872 μL, 8.52 mmol). The $^1$H NMR data, $^{13}$C NMR data, the HRMS-ESI determination of mass, and melting point of Compound 17 are as follows.

The $^1$H NMR (400 MHz, CDCl$_3$): δ 8.47 (1H, d, J 5.2, quinoline-H), 7.99 (1H, d, J 2.0, quinoline-H), 7.82 (1H, d, J 8.8, quinoline-H), 7.43 (1H, dd, J 8.8 and 2.0, quinoline-H), 7.10 (1H, dd, J 8.4 and 2.4, Ar—H), 6.94 (1H, d, J 2.4, Ar—H), 6.88 (1H, d, J 8.4, Ar—H), 6.63 (1H, d, J 5.2, quinoline-H), 6.52 (1H, brs, Ar—OH), 3.85 (2H, s, ArCH$_2$N), 3.84 (2H, t, J 4.2, NCH$_2$CH$_2$OH), 2.77 (2H, t, J 4.2, NCH$_2$CH$_2$OH), 2.73 (2H, q, J 7.2, NCH$_2$CH$_3$), 1.16 (3H, t, J 7.2, NCH$_2$CH$_3$), and the $^{13}$C NMR data (100 MHz, CDCl$_3$): δ 156.3, 151.9, 149.5, 149.2, 135.2, 130.1, 129.0, 125.8, 125.7, 125.3, 123.3, 120.9, 117.4, 101.4, 60.0, 57.6, 55.1, 47.8, 11.1. The HRMS-ESI mass calculated for C$_{20}$H$_{23}$ClN$_3$O$_2^+$ [M+H]$^+$ was 372.14733; and the mass found was 372.14673. The melting point was determined to be about 171.7-172.5° C.

Example 18—Synthesis of Compound 18: 4-(7-iodoquinolin-4-ylamino)-2-diethylaminomethylphenol

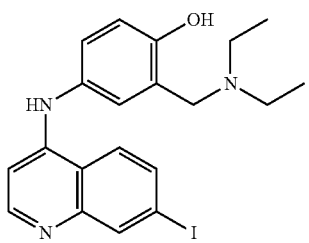

Formula XIX

Compound 18 (125.2 mg, 0.28 mmol, 93% yield) expressed as Formula XIX was obtained as a gray powder using the same procedure as in Example 1, but with the use of diethylamine (881 μL, 8.52 mmol) and 4-chloro-7-iodoquinoline (91.0 mg, 0.32 mmol) instead of dipropargylamine (872 μL, 8.52 mmol) and 4,7-dichloroquinoline (99.0 mg, 0.50 mmol), respectively. The $^1$H NMR data, $^{13}$C NMR data, the HRMS-ESI determination of mass, and melting point of Compound 18 are as follows.

The $^1$H NMR (400 MHz, CDCl$_3$): δ 8.44 (1H, d, J 5.2, quinoline-H), 8.42 (1H, d, J 1.2, quinoline-H), 7.72 (1H, dd, J 8.8 and 1.2, quinoline-H), 7.60 (1H, d, J 8.8, quinoline-H), 7.08 (1H, dd, J 8.4 and 2.4, Ar—H), 6.92 (1H, d, J 2.4, Ar—H), 6.86 (1H, d, J 8.4, Ar—H), 6.64 (1H, d, J 5.2, quinoline-H), 6.55 (1H, brs, Ar—OH), 3.78 (2H, s, ArCH$_2$N), 2.65 (4H, q, J 7.2, NCH$_2$CH$_3$), 1.14 (6H, t, J 7.2, NCH$_2$CH$_3$), and the $^{13}$C NMR data (100 MHz, CDCl$_3$): δ 156.7, 151.5, 149.8, 149.4, 138.8, 133.5, 129.8, 125.5, 125.3, 123.4, 120.8, 118.1, 117.2, 101.5, 95.3, 56.8, 46.4, 11.2. The HRMS-ESI mass calculated for C$_{20}$H$_{23}$IN$_3$O$^+$ [M+H]$^+$ was 448.08803; and the mass found was 448.08638. The melting point was determined to be about 189.7-190.4° C.

Example 19—Synthesis of Compound 19: 4-(7-chloroquinolin-4-ylamino)-2-(3-hydroxy-1-piperidinyl)methylphenol

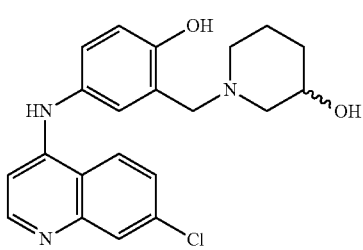

Formula XX

Compound 19 (478.3 mg, 1.25 mmol, 37% yield) expressed as Formula XX was obtained as a pale yellow solid using the same procedure as in Example 1, but with the use of 3-hydroxypiperidine (862 μL, 8.52 mmol) instead of dipropargylamine (872 μL, 8.52 mmol). The $^1$H NMR data, $^{13}$C NMR data, the HRMS-ESI determination of mass, and melting point of Compound 19 are as follows.

The $^1$H NMR (400 MHz, CD$_3$OD): δ 8.30 (1H, d, J 5.2, quinoline-H), 8.24 (1H, d, J 9.2, quinoline-H), 7.83 (1H, d, J 2.0, quinoline-H), 7.46 (1H, dd, J 9.2 and 2.0, quinoline-H), 7.14 (1H, dd, J 8.4 and 2.4, Ar—H), 7.06 (1H, d, J 2.4, Ar—H), 6.85 (1H, d, J 8.4, Ar—H), 6.62 (1H, d, J 5.2, quinoline-H), 3.75 (1H, m, piperidinyl-H), 3.74 (2H, m, ArCH$_2$N), 2.96 (1H, m, piperidinyl-H), 2.74 (1H, m, piperidinyl-H), 2.24 (1H, m, piperidinyl-H), 2.16 (1H, m, piperidinyl-H), 1.88 (2H, m, piperidinyl-H), 1.58 (1H, m, piperidinyl-H), 1.38 (1H, m, piperidinyl-H), and the $^{13}$C NMR data (100 MHz, CD$_3$OD): δ 157.0, 152.5, 152.4, 150.1, 136.6, 132.1, 127.7, 127.3, 126.8, 126.4, 124.5, 124.4, 119.1, 117.7, 101.7, 67.8, 61.5, 61.1, 53.9, 33.5, 32.9. The HRMS-ESI mass calculated for C$_{21}$H$_{23}$ClN$_3$O$_2^+$ [M+H]$^+$ was 384.14733; and the mass found was 384.14693. The melting point was determined to be about 182.5-183.4° C.

Example 20—Synthesis of Compound 20: 6-(4-chlorophenyl)-4-(7-chloroquinolin-4-ylamino)-2-diethylaminomethylphenol

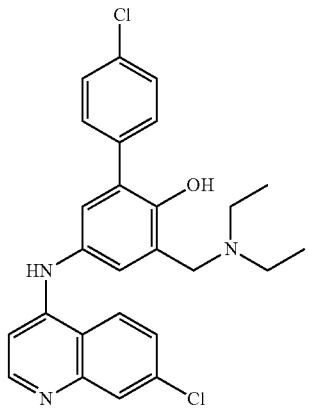

Formula XXI

The synthesis scheme of Compound 20 expressed as Formula XXI is shown in Reaction [II]. 4-Chlorophenol (2551.4 mg, 20 mmol) was suspended in water (20 mL), and 3 N HCl aqueous solution (20 mL) was added. At 0° C., a solution of sodium nitrate (1.38 g, 20 mmol) in 10 mL water was added dropwise to the obtained solution over 20 min. To 5 mL of the obtained solution, p-aminophenol (40a) (1091.3 mg, 10 mmol) and water (16 mL) were added. A solution of titanium trichloride (616.9 mg, 4 mmol) in 1 mL concentrated hydrochloric acid was added dropwise to the solution over 5 min. After stirring for 10 min, a solution of sodium hydroxide (2 g) and sodium thiosulfate (2 g) in 20 mL water was added to the resulting solution. After stirring, ethyl acetate and water were added to the solution, and the mixture was separated into an aqueous layer and organic layer. The aqueous layer was extracted with ethyl acetate, and the extract was combined with the organic layer. The resulting solution was washed thrice with a saturated salt solution and dried over sodium sulfate. Then, the solvent was removed under reduced pressure. The crude product was purified by column chromatography using a mixture of hexane/ethyl acetate (1:1 v/v), affording 4-amino-2-(4-chlorophenyl)phenol (20b) as a yellow crystal (188.5 mg, 0.86 mmol, 43% yield). A mixture of 4-amino-2-(4-chlorophenyl)phenol (20b) (181.8 mg, 0.83 mmol) and 4,7-dichloroquinoline (172.1 mg, 0.87 mmol) was dissolved in ethanol (3 mL), and 3 N HCl aqueous solution (100 μL) was added.

The mixture was refluxed for 10 h. The temperature of the reaction mixture was adjusted to 0° C., and 2% ammonia water (approximately 9 mL) was added under stirring. The precipitated crystals were separated using a Kiriyama funnel.

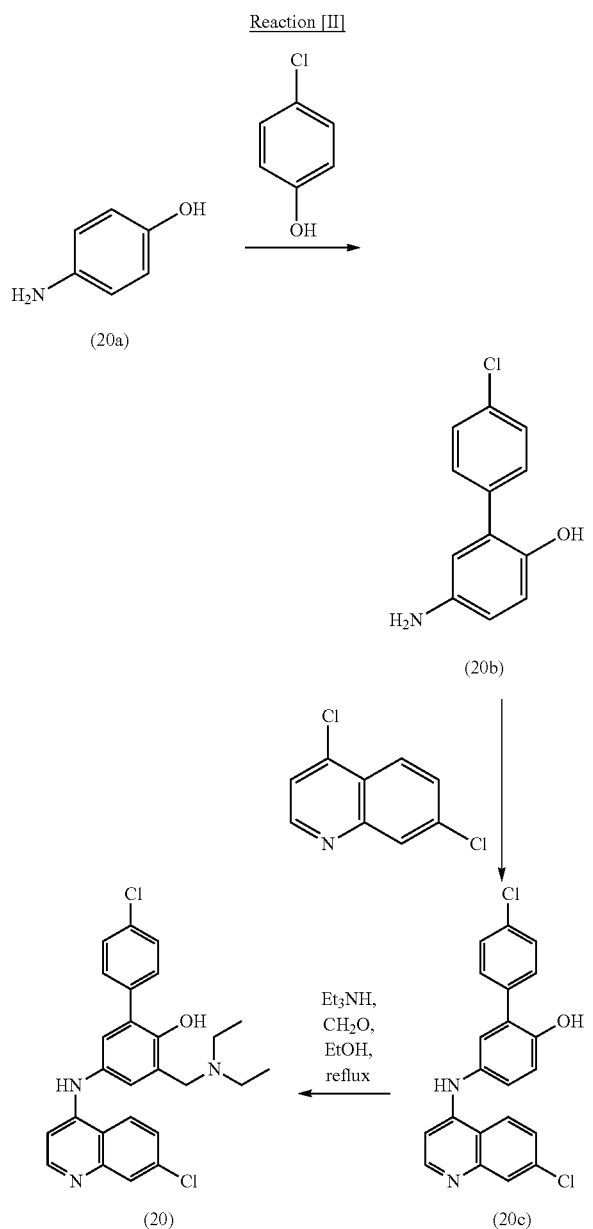

The crude crystals were recrystallized from methanol, affording 4'-chloro-5-[(7-chloro-4-quinolinyl)amino]-[1,1'-biphenyl]-2-ol (20c) (314.3 mg, 0.82 mmol, 99% yield) as a yellow powder. A mixture of the resulting 4'-chloro-5-[(7-chloro-4-quinolinyl)amino]-[1,1'-biphenyl]-2-ol (114.4 mg, 0.3 mmol) and 37% formaldehyde (848 μL, 8.52 mmol) was dissolved in ethanol (5 mL), and diethylamine (1200 μL, 11.6 mmol) was added. The mixture was refluxed for approximately 2 h. The solvent was removed under reduced pressure, and the residue was recrystallized from methanol, affording the title compound (103.4 mg, 0.22 mmol, 74% yield) as a pale yellow powder. The $^1$H NMR data, $^{13}$C NMR data, the HRMS-ESI determination of mass, and melting point of Compound 20 are as follows.

The $^1$H NMR (400 MHz, CDCl$_3$): δ 8.49 (1H, d, J 5.6, quinoline-H), 8.00 (1H, d, J 2.0, quinoline-H), 7.83 (1H, d, J 9.2, quinoline-H), 7.57 (2H, d, J 8.4, Ar—H), 7.43 (1H, dd, J 8.8 and 2.0, quinoline-H), 7.38 (2H, d, J 8.4, Ar—H), 7.16 (1H, d, J 2.8, Ar—H), 6.92 (1H, d, J 2.4, Ar—H), 6.70 (1H, d, J 5.6, quinoline-H), 6.58 (1H, brs, Ar—OH), 3.84 (2H, s, ArCH$_2$N), 2.68 (4H, q, J 7.2, NCH$_2$CH$_3$), 1.14 (6H, t, J 7.2, NCH$_2$CH$_3$), and the $^{13}$C NMR data (100 MHz, CDCl$_3$): δ 153.9, 152.0, 149.6, 149.1, 136.2, 135.2, 133.1, 130.6, 129.9, 129.0, 128.6, 128.3, 125.9, 125.8, 124.6, 123.9, 120.9, 117.4, 101.4, 56.9, 46.3, 11.1. The HRMS-ESI mass calculated for C$_{26}$H$_{26}$Cl$_2$N$_3$O$^+$ [M+H]$^+$: 466.14474; and the mass found was 466.14462. The melting point was determined to be about 205.8-207.4° C.

Example 21—Synthesis of Compound 21: 4-(7-chloroquinolin-4-ylamino)-2-pyrrolidinylmethylphenol

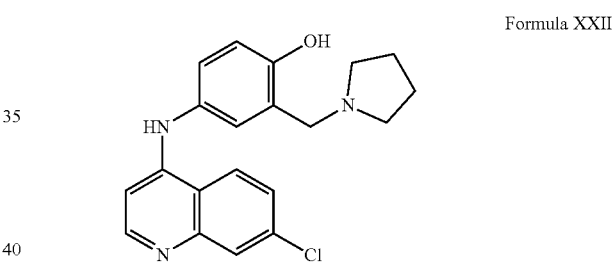

Formula XXII

Compound 21 (402.8 mg, 1.13 mmol, 40% yield) expressed as Formula XXII was obtained as a brown solid using the same procedure as in Example 1, but with the use of pyrrolidine (705 μL, 8.52 mmol) instead of dipropargylamine (872 μL, 8.52 mmol). The $^1$H NMR data, $^{13}$C NMR data, the HRMS-ESI determination of mass, and melting point of Compound 21 are as follows.

The $^1$H NMR (400 MHz, CDCl$_3$): δ 8.45 (1H, d, J 5.2, quinoline-H), 8.00 (1H, d, J 2.0, quinoline-H), 7.86 (1H, d, J 8.4, quinoline-H), 7.42 (1H, dd, J 8.4 and 2.0, quinoline-H), 7.10 (1H, dd, J 8.4 and 2.4, Ar—H), 6.95 (1H, d, J 2.4, Ar—H), 6.87 (1H, d, J 8.4, Ar—H), 6.71 (1H, brs, Ar—OH), 6.63 (1H, d, J 5.2, quinoline-H), 3.84 (2H, s, ArCH$_2$N), 2.68 (4H, m, pyrrolidinyl-H), 1.88 (4H, m, pyrrolidinyl-H), and the $^{13}$C NMR data (100 MHz, CDCl$_3$): δ 156.5, 151.5, 149.5, 149.1, 135.3, 129.7, 128.6, 125.8, 125.6, 124.8, 123.7, 121.1, 117.3, 117.1, 101.3, 58.6, 53.6, 23.7. The HRMS-ESI mass calculated for C$_{20}$H$_{21}$ClN$_3$O$^+$ [M+H]$^+$ was 354.13677; and the mass found was 354.13608. The melting point was determined to be about 188.8-190.0° C.

Example 22—Synthesis of Compound 22: 4-(7-chloroquinolin-4-ylamino)-2-(2-hydroxy-1-pyrrolidinyl)methylphenol

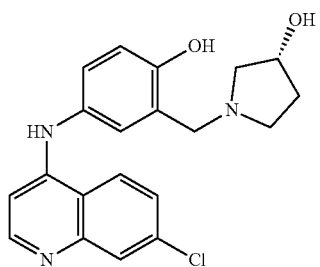

Formula XXIII

Compound 22 (14.2 mg, 0.038 mmol, 2% yield) expressed as Formula XXIII was obtained as a brown solid using the same procedure as in Example 1, but with the use of 3-hydroxypyrrolidine (690 µL, 8.52 mmol) instead of dipropargylamine (872 µL, 8.52 mmol). The $^1$H NMR data, $^{13}$C NMR data, the HRMS-ESI determination of mass, and melting point of Compound 22 are as follows.

The $^1$H NMR (400 MHz, CD$_3$OD): δ 8.30 (1H, d, J 5.2, quinoline-H), 8.24 (1H, d, J 9.2, quinoline-H), 7.83 (1H, s, quinoline-H), 7.46 (1H, d, J 9.2, quinoline-H), 7.14 (1H, d, J 8.4, Ar—H), 7.09 (1H, s, Ar—H), 6.85 (1H, d, J 8.4, Ar—H), 6.62 (1H, d, J 5.2, quinoline-H), 4.41 (1H, m, pyrrolidinyl-H), 3.85 (2H, s, ArCH$_2$N), 2.91 (1H, m, pyrrolidinyl-H), 2.84 (1H, m, pyrrolidinyl-H), 2.68 (1H, m, pyrrolidinyl-H), 2.58 (1H, m, pyrrolidinyl-H), 2.20 (1H, m, pyrrolidinyl-H), 1.80 (1H, m, pyrrolidinyl-H), and the $^{13}$C NMR data (100 MHz, CD$_3$OD): δ 156.9, 152.5, 152.4, 150.1, 136.6, 131.9, 127.7, 127.0, 126.8, 126.4, 125.3, 124.5, 119.1, 117.6, 101.7, 71.6, 63.0, 58.6, 53.2, 35.3. The HRMS-ESI mass calculated for C$_{20}$H$_{21}$ClN$_3$O$_2^+$ [M+H]$^+$ was 370.13168; and the mass found was 370.13091. The melting point was determined to be about 180.8-182.3° C.

Example 23—Synthesis of Compound 23: 4-(7-chloroquinolin-4-ylamino)-2-hexylaminomethylphenol

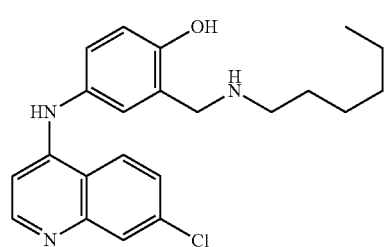

Formula XXIV

Compound 23 (91.8 mg, 0.50 mmol, 12% yield) expressed as Formula XXIV was obtained as a pale yellow solid using the same procedure as in Example 1, but with the use of n-hexylamine (1120 µL, 8.52 mmol) instead of dipropargylamine (872 µL, 8.52 mmol). The 1H NMR data, 13C NMR data, the HRMS-ESI determination of mass, and melting point of Compound 23 are as follows.

The $^1$H NMR (400 MHz, CDCl$_3$): δ 8.41 (1H, d, J 5.6, quinoline-H), 7.95 (1H, d, J 2.0, quinoline-H), 7.88 (1H, d, J 8.8, quinoline-H), 7.36 (1H, dd, J 8.8 and 2.0, quinoline-H), 7.07 (1H, dd, J 8.4 and 2.4, Ar—H), 6.99 (1H, brs, Ar—OH), 6.92 (1H, d, J 2.4, Ar—H), 6.86 (1H, d, J 8.4, Ar—H), 6.60 (1H, d, J 5.6, quinoline-H), 3.97 (2H, s, ArCH$_2$N), 2.68 (2H, q, J 7.2, NCH$_2$CH$_2$CH$_2$CH$_2$CH$_2$CH$_3$), 1.55 (2H, m, NCH$_2$CH$_2$CH$_2$CH$_2$CH$_2$CH$_3$), 1.30 (6H, m, NCH$_2$CH$_2$CH$_2$CH$_2$CH$_2$CH$_3$), 0.89 (3H, t, J 7.2, NCH$_2$CH$_2$CH$_2$CH$_2$CH$_2$CH$_3$), and the $^{13}$C NMR data (100 MHz, CDCl$_3$): δ 156.7, 151.8, 149.6, 149.4, 135.2, 130.0, 128.5, 125.6, 125.2, 123.8, 121.4, 117.5, 117.4, 101.3, 52.5, 50.5, 48.9, 31.6, 29.5, 26.8, 22.6, 14.0. The HRMS-ESI mass calculated for C$_{22}$H$_{27}$ClN$_3$O$^+$ [M+H]$^+$ was 384.18372; and the mass found was 384.18296. The melting point was determined to be about 135.7-137.2° C.

Example 24—Synthesis of Compound 24: 4-(7-chloroquinolin-4-ylamino)-4-morpholinylmethylphenol

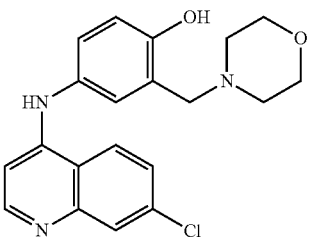

Formula XXV

Compound 24 (1079.8 mg, 2.94 mmol, 50% yield) expressed as Formula XXV was obtained as a white solid using the same procedure as in Example 1, but with the use of morpholine (887 µL, 8.52 mmol) instead of dipropargylamine (872 µL, 8.52 mmol). The 1H NMR data, 13C NMR data, the HRMS-ESI determination of mass, and melting point of Compound 24 are as follows.

The $^1$H NMR (400 MHz, CDCl$_3$): δ 8.47 (1H, d, J 5.2, quinoline-H), 8.00 (1H, d, J 2.0, quinoline-H), 7.82 (1H, d, J 8.8, quinoline-H), 7.42 (1H, dd, J 8.8 and 2.0, quinoline-H), 7.13 (1H, dd, J 8.4 and 2.4, Ar—H), 6.96 (1H, d, J 2.4, Ar—H), 6.90 (1H, d, J 8.4, Ar—H), 6.62 (1H, d, J 5.2, quinoline-H), 3.79 (4H, m, morpholinyl-H), 3.73 (2H, s, ArCH$_2$N), 2.61 (4H, m, morpholinyl-H), and the $^{13}$C NMR data (100 MHz, CDCl$_3$): δ 155.8, 151.9, 149.6, 149.1, 135.2, 130.4, 129.0, 125.9, 125.8, 125.6, 121.9, 121.0, 117.4, 117.3, 101.4, 66.8, 61.7, 52.9. The HRMS-ESI mass calculated for C$_{20}$H$_{21}$ClN$_3$O$_2^+$ [M+H]$^+$ was 370.13168; and the mass found was 370.13085. The melting point was determined to be about 21.58-216.4° C.

Example 25—Synthesis of Compound 25: 4-(7-chloroquinolin-4-ylamino)-2-(butylmethylamino)methylphenol

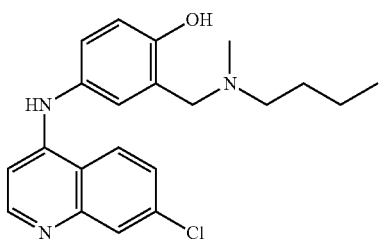

Formula XXVI

Compound 25 (539.4 mg, 1.46 mmol, 34% yield) expressed as Formula XXVI was obtained as a pale yellow solid using the same procedure as in Example 1, but with the use of N-methylbutylamine (1004 μL, 8.52 mmol) instead of dipropargylamine (872 μL, 8.52 mmol). The 1H NMR data, 13C NMR data, the HRMS-ESI determination of mass, and melting point (mp) of Compound 25 are as follows.

The $^1$H NMR (400 MHz, CDCl$_3$): δ 8.47 (1H, d, J 5.2, quinoline-H), 8.00 (1H, d, J 2.0, quinoline-H), 7.82 (1H, d, J 9.2, quinoline-H), 7.42 (1H, dd, J 9.2 and 2.0, quinoline-H), 7.09 (1H, dd, J 8.4 and 2.4, Ar—H), 6.92 (1H, d, J 2.4, Ar—H), 6.87 (1H, d, J 8.4, Ar—H), 6.62 (1H, d, J 5.2, quinoline-H), 6.55 (1H, brs, Ar—OH), 3.70 (2H, s, ArCH$_2$N), 2.51 (2H, m, NCH$_2$CH$_2$CH$_2$CH$_3$), 2.31 (3H, s, NCH$_3$), 1.56 (2H, m, NCH$_2$CH$_2$CH$_2$CH$_3$), 1.36 (2H, m, NCH$_2$CH$_2$CH$_2$CH$_3$), 0.94 (3H, t, J 7.2, NCH$_2$CH$_2$CH$_2$CH$_3$), and the $^{13}$C NMR data (100 MHz, CDCl$_3$): δ 156.5, 152.0, 149.6, 149.2, 135.1, 129.9, 129.0, 125.7, 125.7, 125.3, 123.2, 121.0, 117.4, 117.1, 101.4, 61.3, 56.9, 41.2, 29.0, 20.4, 13.9. The HRMS-ESI mass calculated for C$_{21}$H$_{25}$ClN$_3$O$^+$ [M+H]$^+$ was 370.16807; and the mass found was 370.16741. The melting point was determined to be about 159.6-160.6° C.

Example 26—Synthesis of Compound 26: 4-(7-chloroquinolin-4-ylamino)-2-dipropylaminomethylphenol

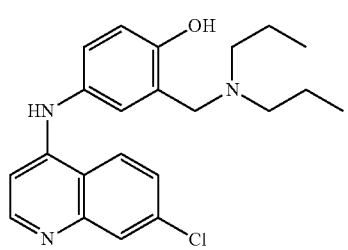

Formula XXVII

Compound 26 (732.8 mg, 1.91 mmol, 46% yield) expressed as Formula XXVII was obtained as a pale yellow solid using the same procedure as in Example 1, but with the use of N-dipropylamine (1171 μL, 8.52 mmol) instead of dipropargylamine (872 μL, 8.52 mmol). The 1H NMR data, 13C NMR data, the HRMS-ESI determination of mass, and melting point of Compound 26 are as follows.

The $^1$H NMR (400 MHz, CDCl$_3$): δ 8.48 (1H, d, J 5.2, quinoline-H), 8.00 (1H, d, J 2.4, quinoline-H), 7.82 (1H, d, J 8.8, quinoline-H), 7.42 (1H, dd, J 8.8 and 2.4, quinoline-H), 7.09 (1H, dd, J 8.4 and 2.0, Ar—H), 6.92 (1H, d, J 2.4, Ar—H), 6.86 (1H, d, J 8.4, Ar—H), 6.63 (1H, d, J 5.2, quinoline-H), 6.57 (1H, brs, Ar—OH), 3.77 (2H, s, ArCH$_2$N), 2.51 (4H, m, NCH$_2$CH$_2$CH$_3$), 1.56 (4H, m, NCH$_2$CH$_2$CH$_3$), 0.92 (6H, t, J 7.2, NCH$_2$CH$_2$CH$_3$), and the $^{13}$C NMR data (100 MHz, CDCl$_3$): δ 156.6, 152.0, 149.6, 149.3, 135.1, 129.9, 129.0, 125.7, 125.5, n125.3, 123.5, 121.0, 117.4, 117.1, 101.4, 58.1, 55.5, 19.5, 11.8. The HRMS-ESI mass calculated for C$_{22}$H$_{27}$ClN$_3$O$^+$ [M+H]$^+$ was 384.18372; and the mass found was 384.18302. The melting point was determined to be about 163.2-164.3° C.

Example 27—Synthesis of—Compound 27: 4-(7-chloroquinolin-4-ylamino)-2-bis(2-propen-1-yl)aminomethylphenol

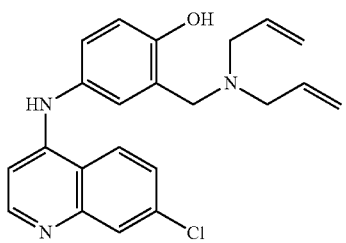

Formula XXVIII

Compound 27 (175.8 mg, 0.46 mmol, 10% yield) expressed as Formula XXVIII was obtained as a white solid using the same procedure as in Example 1, but with the use of diallylamine (1048 μL, 8.52 mmol) instead of dipropargylamine (872 μL, 8.52 mmol). The 1H NMR data, 13C NMR data, the HRMS-ESI determination of mass, and melting point of Compound 27 are as follows.

The $^1$H NMR (400 MHz, CD$_3$OD): δ 8.31 (1H, d, J 5.6, quinoline-H), 8.26 (1H, d, J 9.2, quinoline-H), 7.84 (1H, d, J 1.2, quinoline-H), 7.47 (1H, dd, J 9.2 and 1.2, quinoline-H), 7.15 (1H, dd, J 8.4 and 2.0, Ar—H), 7.07 (1H, d, J 2.0, Ar—H), 6.86 (1H, d, J 8.4, Ar—H), 6.63 (1H, d, J 5.6, quinoline-H), 5.95 (2H, m, NCH$_2$CHCH$_2$), 5.27 (4H, m, NCH$_2$CHCH$_2$), 3.81 (2H, s, ArCH$_2$N), 3.23 (4H, d, J 6.4, NCH$_2$CHCH$_2$), and the $^{13}$C NMR data (100 MHz, CD$_3$OD): δ 157.0, 152.5, 152.4, 150.1, 136.6, 135.0, 132.2, 127.7, 127.3, 126.8, 126.4, 124.9, 124.6, 119.8, 119.1, 117.7, 101.8, 57.0, 56.7. The HRMS-ESI mass calculated for C$_{22}$H$_{23}$ClN$_3$O$^+$ [M+H]$^+$ was 380.15242; and the mass found was 380.15179. The melting point was determined to be about 161.4-162.8° C.

Example 28—Synthesis of Compound 28: 4-(7-chloroquinolin-4-ylamino)-2-dibutylaminomethylphenol

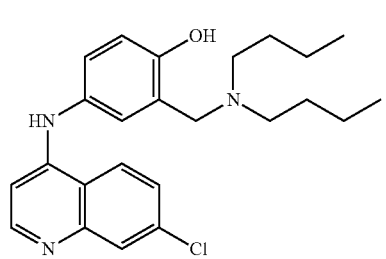

Formula XXIX

Compound 28 (660.2 mg, 1.60 mmol, 33% yield) expressed as Formula XXIX was obtained as a white solid using the same procedure as in Example 1, but with the use of dibutylamine (1457 μL, 8.52 mmol) instead of dipropargylamine (872 μL, 8.52 mmol). The 1H NMR data, 13C NMR data, the HRMS-ESI determination of mass, and melting point of Compound 28 are as follows.

The $^1$H NMR (400 MHz, CDCl$_3$): δ 8.48 (1H, d, J 5.2, quinoline-H), 8.00 (1H, d, J 2.4, quinoline-H), 7.82 (1H, d, J 8.8, quinoline-H), 7.42 (1H, dd, J 8.8 and 2.4, quinoline-H), 7.09 (1H, dd, J 8.4 and 2.0, Ar—H), 6.92 (1H, d, J 2.0, Ar—H), 6.86 (1H, d, J 8.4, Ar—H), 6.62 (1H, d, J 5.2, quinoline-H), 6.54 (1H, brs, Ar—OH), 3.77 (2H, s, ArCH$_2$N), 2.54 (4H, m, NCH$_2$CH$_2$CH$_2$CH$_3$), 1.56 (4H, m, NCH$_2$CH$_2$CH$_2$CH$_3$), 1.32 (4H, m, NCH$_2$CH$_2$CH$_2$CH$_3$), 0.92 (6H, t, J 7.2, NCH$_2$CH$_2$CH$_2$CH$_3$), and the $^{13}$C NMR data (100 MHz, CDCl$_3$): δ 156.6, 152.0, 149.6, 149.3, 135.1, 129.9, 129.0, 125.7, 125.6, 125.3, 123.5, 121.0, 117.4, 117.1, 101.4, 58.0, 53.2, 28.4, 20.6, 14.0. The HRMS-ESI mass calculated for $C_{24}H_{31}ClN_3O^+$ [M+H]$^+$: 412.21502; and the mass found was 412.21430. The melting point was determined to be about 152.9-153.2° C.

Example 29—Synthesis of Compound 29: 4-(7-chloroquinolin-4-ylamino)-2-(ethylpropylamino)methylphenol

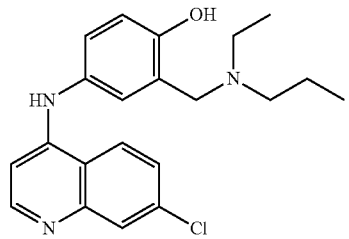

Formula XXX

Compound 29 (363.7 mg, 0.98 mmol, 28% yield) expressed as Formula XXX was obtained as a white solid using the same procedure as in Example 1, but with the use of N-ethylpropylamine (1032 μL, 8.52 mmol) instead of dipropargylamine (872 μL, 8.52 mmol). The 1H NMR data, 13C NMR data, the HRMS-ESI determination of mass, and melting point of Compound 29 are as follows.

The $^1$H NMR (400 MHz, CDCl$_3$): δ 8.48 (1H, d, J 5.2, quinoline-H), 7.99 (1H, d, J 2.0, quinoline-H), 7.82 (1H, d, J 9.2, quinoline-H), 7.41 (1H, dd, J 9.2 and 2.0, quinoline-H), 7.08 (1H, dd, J 8.4 and 2.0, Ar—H), 6.92 (1H, d, J 2.0, Ar—H), 6.86 (1H, d, J 8.4, Ar—H), 6.63 (1H, d, J 5.2, quinoline-H), 6.57 (1H, brs, Ar—OH), 3.77 (2H, s, ArCH$_2$N), 2.64 (2H, m, NCH$_2$CH$_3$), 2.51 (2H, m, NCH$_2$CH$_2$CH$_3$), 1.59 (2H, m, NCH$_2$CH$_2$CH$_3$), 1.12 (3H, t, J 7.2, NCH$_2$CH$_3$), 0.93 (3H, t, J 7.2, NCH$_2$CH$_2$CH$_3$), and the $^{13}$C NMR data (100 MHz, CDCl$_3$): δ 156.6, 152.0, 149.6, 149.3, 135.1, 129.9, 129.0, 125.7, 125.5, 125.3, 123.4, 121.0, 117.4, 117.1, 101.4, 57.4, 54.9, 46.9, 19.7, 11.8, 12.0. The HRMS-ESI mass calculated for $C_{21}H_{25}ClN_3O^+$ [M+H]$^+$ was 370.16807; and the mass found was 370.16782. The melting point was determined to be about 174.4-175.8° C.

Example 30—Synthesis of Compound 30: 4-(7-iodoquinolin-4-ylamino)-2-dimethylaminomethylphenol

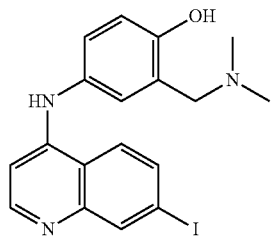

Formula XXXI

Compound 30 expressed as Formula XXXI with molecular weight of 419.26 was obtained using the same procedure as in Example 1, but with the use of disubstituted amine and 4-chloro-7-iodoquinoline instead of dipropargylamine and 4,7-dichloroquinoline, respectively.

Example 31—Synthesis of Compound 31: 4-(7-iodoquinolin-4-ylamino)-2-ethylmethylaminomethylphenol

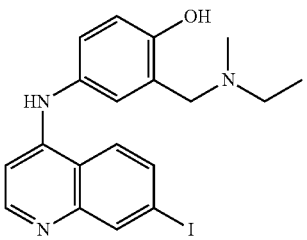

Formula XXXII

Compound 31 expressed as Formula XXXII with molecular weight of 433.29 was obtained using the same procedure as in Example 1, but with the use of the corresponding disubstituted amine and 4-chloro-7-iodoquinoline instead of dipropargylamine and 4,7-dichloroquinoline, respectively.

Example 32—Synthesis of Compound 32: 4-(7-iodoquinolin-4-ylamino)-2-isopropylmethylaminomethylphenol

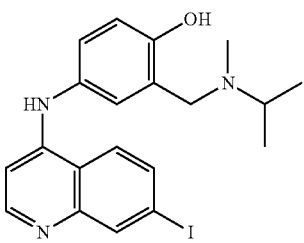

Formula XXXIII

Compound 32 expressed as Formula XXXIII with molecular weight of 447.31 was obtained using the same procedure as in Example 1, but with the use of the corresponding disubstituted amine and 4-chloro-7-iodoquinoline instead of dipropargylamine and 4,7-dichloroquinoline, respectively.

Example 33—Synthesis of Compound 33: 4-(7-iodoquinolin-4-ylamino)-2-tert-butylmethylaminomethylphenol

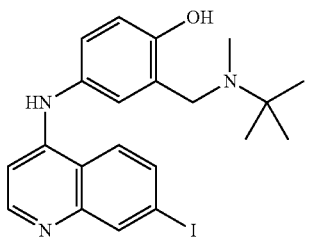

Formula XXXIV

Compound 33 expressed as Formula XXXIV with molecular weight of 461.34 was obtained using the same procedure as in Example 1, but with the use of the corresponding disubstituted amine and 4-chloro-7-iodoquinoline instead of dipropargylamine and 4,7-dichloroquinoline, respectively.

Example 34—Synthesis of Compound 34: 4-(7-iodoquinolin-4-ylamino)-2-methylpropylaminomethylphenol

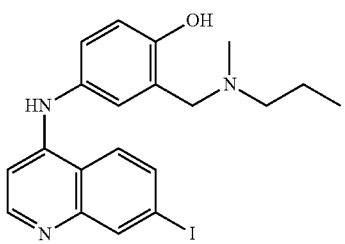

Formula XXXV

Compound 34 expressed as Formula XXXV with molecular weight of 447.31 was obtained using the same procedure as in Example 1, but with the use of the corresponding disubstituted amine and 4-chloro-7-iodoquinoline instead of dipropargylamine and 4,7-dichloroquinoline, respectively.

Example 35—Synthesis of Compound 35: 4-(7-iodoquinolin-4-ylamino)-2-butylmethylaminomethylphenol

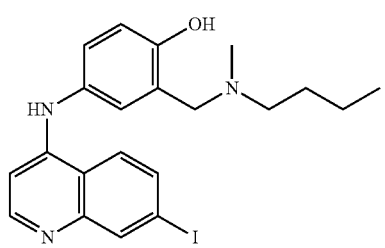

Formula XXXVI

Compound 35 expressed as Formula XXXVI with molecular weight of 461.34 was obtained using the same procedure as in Example 1, but with the use of the corresponding disubstituted amine and 4-chloro-7-iodoquinoline instead of dipropargylamine and 4,7-dichloroquinoline, respectively.

Example 36—Synthesis of Compound 36: 4-(7-iodoquinolin-4-ylamino)-2-methylpentylaminomethylphenol

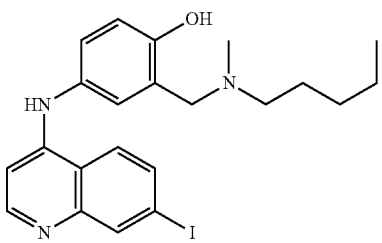

Formula XXXVII

Compound 36 expressed as Formula XXXVII with molecular weight of 475.36 was obtained using the same procedure as in Example 1, but with the use of the corresponding disubstituted amine and 4-chloro-7-iodoquinoline instead of dipropargylamine and 4,7-dichloroquinoline, respectively.

Example 37—Synthesis of Compound 37: 4-(7-iodoquinolin-4-ylamino)-2-hexylmethylaminomethylphenol

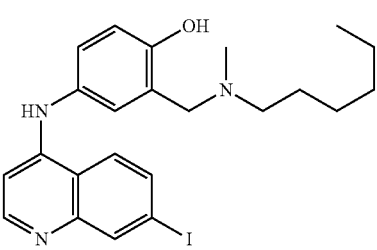

Formula XXXVIII

Compound 37 expressed as Formula XXXVIII with molecular weight of 489.39 was obtained using the same procedure as in Example 1, but with the use of the corresponding disubstituted amine and 4-chloro-7-iodoquinoline instead of dipropargylamine and 4,7-dichloroquinoline, respectively.

Example 38—Synthesis of Compound 38: 4-(7-iodoquinolin-4-ylamino)-2-methyloctylaminomethylphenol

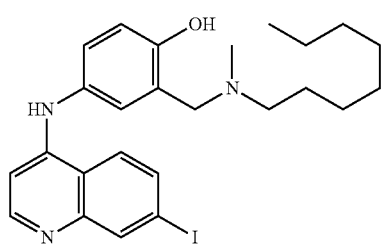

Formula XXXIX

Compounds 38 expressed as Formula XXXIX with molecular weight of 517.44 was obtained using the same procedure as in Example 1, but with the use of the corresponding disubstituted amine and 4-chloro-7-iodoquinoline instead of dipropargylamine and 4,7-dichloroquinoline, respectively.

Example 39—Synthesis of Compound 39: 4-(7-iodoquinolin-4-ylamino)-2-ethyl(2-hydroxyethyl)aminomethylphenol

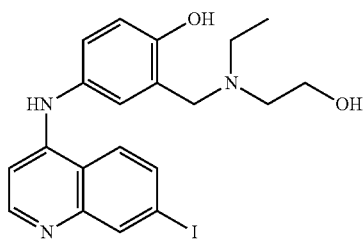

Formula XL

Compounds 39 expressed as Formula XL with molecular weight of 463.31 was obtained using the same procedure as in Example 1, but with the use of the corresponding disubstituted amine and 4-chloro-7-iodoquinoline instead of dipropargylamine and 4,7-dichloroquinoline, respectively.

Example 40—Synthesis of Compound 40: 4-(7-iodoquinolin-4-ylamino)-2-ethylpropylaminomethylphenol

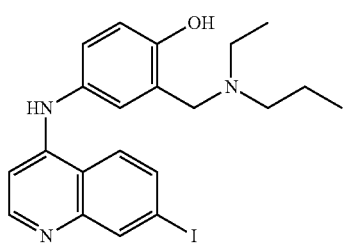

Formula XLI

Compounds 40 expressed as Formula XLI with molecular weight of 461.34 obtained using the same procedure as in Example 1, but with the use of the corresponding disubstituted amine and 4-chloro-7-iodoquinoline instead of dipropargylamine and 4,7-dichloroquinoline, respectively.

Example 41—Synthesis of Compound 41: 4-(7-iodoquinolin-4-ylamino)-2-ethylbutylaminomethylphenol

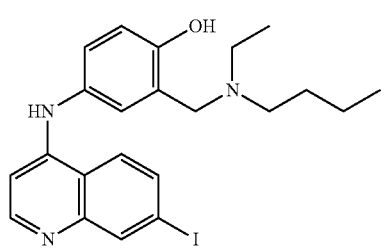

Formula XLII

Compounds 41 expressed as Formula XLII with molecular weight of 475.36 obtained using the same procedure as in Example 1, but with the use of the corresponding disubstituted amine and 4-chloro-7-iodoquinoline instead of dipropargylamine and 4,7-dichloroquinoline, respectively.

Example 42—Synthesis of Compound 42: 4-(7-iodoquinolin-4-ylamino)-2-(1-pyrrolidinylmethyl)phenol

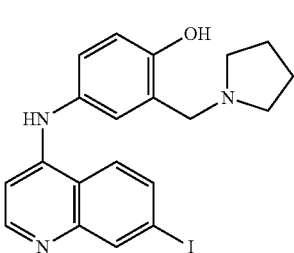

Formula XLIII

Compound 42 expressed as Formula XLIII with molecular weight of 445.30 was obtained using the same procedure as in Example 1, but with the use of the corresponding disubstituted amine and 4-chloro-7-iodoquinoline instead of dipropargylamine and 4,7-dichloroquinoline, respectively.

Example 43—Synthesis of Compound 43: 4-(7-iodoquinolin-4-ylamino)-2-(1-piperidinylmethyl)phenol

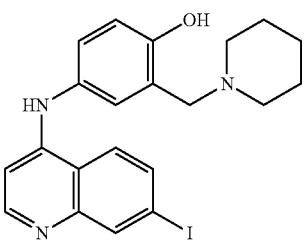

Formula XLIV

Compound 43 expressed as Formula XLIV with molecular weight of 459.32 was obtained using the same procedure as in Example 1, but with the use of the corresponding disubstituted amine and 4-chloro-7-iodoquinoline instead of dipropargylamine and 4,7-dichloroquinoline, respectively.

Example 44—Synthesis of Compound 44: 4-(7-iodoquinolin-4-ylamino)-2-(4-morpholinylmethyl)phenol

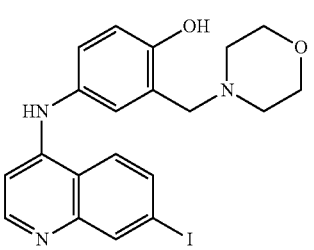

Formula XLV

Compound 44 expressed as Formula XLV with molecular weight of 461.30 was obtained using the same procedure as in Example 1, but with the use of the corresponding disubstituted amine and 4-chloro-7-iodoquinoline instead of dipropargylamine and 4,7-dichloroquinoline, respectively.

Example 45—Synthesis of Compound 45: 4-(7-iodoquinolin-4-ylamino)-2-(4-thiamorpholinylmethyl)phenol

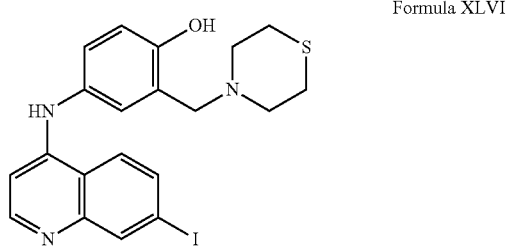 [SMILES: Oc1ccc(Nc2ccnc3cc(I)ccc23)cc1CN1CCSCC1]

Formula XLVI

Compounds 45 expressed as Formula XLVI with molecular weight of 477.36 obtained using the same procedure as in Example 1, but with the use of the corresponding disubstituted amine and 4-chloro-7-iodoquinoline instead of dipropargylamine and 4,7-dichloroquinoline, respectively.

Example 46

Cells and Reagents

Huh7 cells (from Dr. Stanley Lemon, University of North Carolina, N.C., USA) and Vero-E6 cells (from Center for Disease Control, Atlanta, Ga., USA) were maintained in Dulbecco's modified Eagle's medium (DMEM) supplemented with 10% fetal bovine serum (FBS) and 1% penicillin/streptomycin solution. For immunostaining, Hoechst33342 dye was purchased from Life Technologies.

EBOV-GFP Cultivation and Infection

A recombinant Ebolavirus encoding a GFP reporter gene (EBOV-GFP) was provided by Dr. Heinz Feldman (Rocky Mountain Laboratories, National Institute of Health, Hamilton, Mont.). The virus was cultivated on Vero-E6 cells by infection at an MOI of approximately 0.1. Culture supernatants were collected after 5 days, and clarified by centrifugation at 2000×g for 15 min. The virus was concentrated by ultracentrifugation at 82,700×g for 2 h pelleting through a 20% sucrose cushion and resuspended in PBS. Virus titer was determined by serial dilution on Vero-E6 cells. After 24 h-incubation, the cells were fixed in 10% formalin for >24 h, washed with PBS, stained with Hoechst33342 dye and imaged by a Nikon Ti Eclipse inverted microscope with a 4× lens. Counting of the cell nuclei and GFP-positive foci was performed using Cell Profiler image analysis software (Broad Institute, MIT, Boston, Mass.) and customized analysis pipeline. For infection assays, Huh7 cells were plated in 384 well plates and incubated overnight at 37° C. After pretreated with drugs in 2-fold serial dilutions for 1-5 hours, cells were challenged with EBOV-GFP at an MOI of 0.01 for 24 h. This time corresponded to approximately one round of replication and allowed for accumulation of enough GFP to be detected in infected cells. All infected cells were fixed and analyzed as described above. All experiments with replication competent Ebolavirus were performed in a biosafety level 4 (BSL4) laboratory at Texas Biomedical Research Institute, San Antonio, USA.

Cytotoxicity Measurement

Drug cytotoxicity was measured using CellTiter-Glo Luminescent Cell Viability Assay (Promega, Madison, Wis., USA) following the manufacturer's protocol. After Huh7 cells were incubated with inhibitors for 24 h, the substrate in the assay buffer was added to the culture plates and incubated for additional 10 min. Luminescence was measured using a 96-well plate luminometer (Promega).

To identify potent anti-Ebolavirus compounds, compounds structurally related to amodiaquine were synthesized as described in Examples 1-29 and then tested for efficacy for inhibition of virus infection of Huh7 cells. A cytotoxicity assay was then performed using Cell Titer Glo assay system that measures cell viability. These compounds were tested for antiviral activity using replication competent Ebolavirus. The virus was genetically modified to express a GFP protein as reporter for virus infection. Infected cells were detected by GFP expression and infection was compared between treated and untreated cells. Huh7 cells were chosen as they are derived from human liver, which is one of the major infection target tissues in vivo and compounds that are effective in this cell type are more likely to be effective in vivo. Of the 29 amodiaquine derivatives, described herein as Formulae [II]-[XXX], the greatest potency compounds were Compound 7, Compound 18, Compound 23 and Compound 28 with $IC_{50}$ values of 0.73, 0.64, 0.29 and 0.72 μM respectively, which were 3-7 fold more active than amiodiaquine with an $IC_{50}$ of 2.13 μM (Table 1). A score of 1.5 μM was set as the cut off for better potency than amiodiaquine as this corresponded to its $IC_{50}$ minus twice the SD of the measurement (2× σ). Thus, 14 compounds showed greater antiviral activity over amodiaquine.

The majority of the potent compounds including Compound 8, Compound 9, Compound 11, Compound 14, Compound 15, Compound 21, Compound 23, Compound 25, Compound 26, Compound 28 and Compound 29 had modified alkyl chains (R1) extending from the aminomethyl group bonded to the phenol group (Table 1). Extension of at least one of the alkyl chains increased potency. However, existence of triple covalent bonds (compound 1) or benzene rings (compound 3) had reduced antiviral activity. Permitted substitutions on the alkyl chains that did not decrease potency were amino groups such as Compound 13 or hydroxyl groups such as Compound 17, Compound 19 and Compound 22.

The electronegativity of halogens bounded to position 7 (R2) of the quinoline ring appeared to inversely correspond to potency. Fluorine (Compound 5), with the highest electronegativity was weaker than amiodiaquine, which has a chlorine at this position, while bromine (Compound 4) and iodine (Compound 18), which have the lowest electronegativity, had improved potency of 1.4 and 3.3-fold respectively (Table 1).

Phenol ring adducts (R3) such as chlorobenzene had a positive effect on the antiviral activity. This was highlighted by 1.6-fold greater antiviral activity of Compound 20 than amodiaquine (Table 1).

Compounds with a phenyl ring or benzene ring attached to the quinoline ring through position 3 (R4), such as compound 7, which has a methoxy group, also showed greater potency (2.9-fold) against Ebolavirus infection (Table 1). This structure is similar to the structures of pyronaridine and quinacrine, which are antimalarial agents and were shown to have anti-Ebolavirus activities.

Selectivity index (SI) provides a measure of potency relative to cell toxicity. It is calculated by dividing the concentration at which the compound has 50% activity ($IC_{50}$) by the concentration at which toxicity reaches 50% ($CC_{50}$). SI values were calculated for 14 compounds with greater potency than amiodiaquine as described above (Table 2). Cytotoxicity was evaluated by measuring cell viability after 1 day incubation with the compounds, as done for the infection assays. The SI for amiodiaquine was 37. Compound 18 and Compound 28 showed decreased cytotoxicity with $CC_{50}$ greater than 100 µM and yielded SI>130 (Table 2). Compound 11, Compound 14, Compound 25, Compound 26 and Compound 29 also gave SI values greater than amiodiaquine.

The initial screening demonstrated that the alkyl chain at R1 and the halogen were strong factors of compound potency against Ebola virus without negatively affecting cytotoxicity. Importantly, these two structural features can be independently modified. According to these structure-activity relationship analyses, the 2nd set of derivatives was synthesized. Since the initial screening revealed that iodine substitution at R2 increased antiviral activity, all later compounds possessed an iodine substitution combined with a variety of alkyl chains at R1. As expected, most of the derivatives efficiently blocked Ebola virus infection (Table 1). Importantly, some were more potent than compound 18, previously the most potent compound. Consistent with the initial screening results, extension of at least one of the alkyl chains at R1 increased antiviral activity. Cytotoxicity tests revealed that most of the compounds showed low toxicity (Table 2). Compound 34, Compound 36, Compound 37, Compound 38, Compound 39, Compound 40 and Compound 43 yielded SIs>200 and appeared to have higher potential as anti-Ebola virus compounds than the potent compounds in the initial screening.

TABLE 2

Selectivity indexes of potent amodiaquine derivatives

| Compound | $IC_{50}$ (µM) | $CC_{50}$ (µM) | Selectivity index |
|---|---|---|---|
| Amodiaquine | 2.13 | 78.95 | 37 |
| 7 | 0.73 | 14.75 | 20 |
| 8 | 1.46 | 39.18 | 27 |
| 9 | 1.21 | 26.09 | 22 |
| 11 | 1.46 | 60.5 | 41 |
| 14 | 1.22 | >100 | >82 |
| 15 | 1.28 | 41.77 | 33 |
| 18 | 0.64 | >100 | >156 |
| 20 | 1.31 | 19.48 | 15 |
| 21 | 1.09 | 33.16 | 30 |
| 23 | 0.29 | 5.18 | 18 |
| 25 | 0.86 | 65.91 | 77 |
| 26 | 0.94 | >100 | >106 |
| 28 | 0.72 | >100 | >139 |
| 29 | 1.39 | >100 | >72 |
| 30 | 0.69 | >100 | >145 |
| 31 | 0.62 | >100 | >161 |
| 32 | 0.29 | 38.35 | 132 |
| 33 | 0.30 | 32.34 | 108 |
| 34 | 0.43 | >100 | >233 |
| 35 | 0.44 | 66.13 | 150 |
| 36 | 0.37 | >100 | >270 |
| 37 | 0.39 | >100 | >256 |
| 38 | 0.26 | >100 | >385 |
| 39 | 0.41 | >100 | >244 |
| 40 | 0.36 | >100 | >278 |
| 41 | 0.41 | 60.36 | 147 |
| 42 | 0.66 | 35.34 | 54 |
| 43 | 0.37 | >100 | >270 |
| 44 | 1.59 | >100 | >63 |
| 45 | 1.95 | >100 | >51 |

As anticipated, amodiaquine, a well-tolerated drug used for treatment of malaria, demonstrated anti-Ebolavirus activity. Surprisingly, certain modifications of the amodiaquine structure generated compounds with up to 8 times the potency of the parent. Certain specific structure-activity relationships were determined for potent anti-Ebolavirus activity. Some of the modifications, which enhanced the antiviral effects, were independent of each other. The length of the alkyl chains extending from the aminomethyl group bonded to the phenol group and the electronegativity of the halogen bounded to position 7 of the quinoline ring enhanced the compound potency against Ebolavirus. Many derivatives with the modifications showed similar or less cytotoxicity but greater antiviral potency than amodiaquine. These modifications, when combined, further improved potency toward the submicromolar range. In certain embodiments, the pharmaceutical composition can contain one or more of the compounds described herein that have a selectivity index greater than amiodiaquine. In certain embodiments, the pharmaceutical composition can contain one or more of the compounds described herein that have a selectivity index greater than 50. In certain embodiments, the pharmaceutical composition can contain one or more of the compounds described herein that have a selectivity index greater than 100. In certain embodiments, the pharmaceutical composition can contain one or more of the compounds described herein that have a selectivity index greater than 200.

In certain embodiments, compounds described here can be developed for further potency or targeted delivery. In certain embodiments, these compounds can be used to treat or ameliorate the symptoms of both Ebolavirus disease and malaria. As these diseases affect people in overlapping regions of Africa and each is easily confused in its early phase, such a drug could be highly advantageous in providing treatment when a quick and specific diagnosis is not available.

Further modifications and alternative embodiments of various aspects of the compositions and methods disclosed here will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described here are to be taken as examples of embodiments. Elements and materials may be substituted for those illustrated and described here, parts and processes may be reversed or omitted, and certain features of the embodiments may be utilized independently, all as would be apparent to one skilled in the art after having the benefit of this description of the embodiments. Changes may be made in the elements described here without departing from the spirit and scope of the embodiments as described in the following claims.

The foregoing descriptions of methods, compositions, and results obtained using them are provided merely as illustrative examples. Descriptions of the methods are not intended to require or imply that the steps of the various embodiments must be performed in the order presented. As will be appreciated by one of ordinary skill in the art, the steps in the foregoing embodiments may be performed in any order. Words such as "then" are not intended to limit the order of the steps; these words are simply used to guide the reader through the description of the methods. Many of the operations may be performed in parallel or concurrently. In addition, the order of the operations may be re-arranged. A process may correspond to a method, a function, a procedure, a subroutine, a subprogram, etc. Various modifications to these embodiments will be readily apparent to those skilled in the art, and the generic principles defined here may be applied to other embodiments without departing from the spirit or scope of the disclosure.

What is claimed is:

1. A method for treating an Ebolavirus infection in a subject in need of treating the Ebolavirus infection, the method comprising administering to the subject a therapeutically effective amount of a pharmaceutical composition comprising a compound represented by the general formula I:

General formula I wherein $R_2$ is an iodine, $R_3$ is a hydrogen, $R_4$ is a hydrogen, and $R_1$ is selected from the group consisting of:

2. The method of claim 1, wherein the pharmaceutical composition contains 4-(7-iodoquinolin-4-ylamino)-2-methylpropylaminomethylphenol.

3. The method of claim 1, wherein the pharmaceutical composition contains 4-(7-iodoquinolin-4-ylamino)-2-methylpentylaminomethylphenol.

4. The method of claim 1, wherein the pharmaceutical composition contains 4-(7-iodoquinolin-4-ylamino)-2-hexylmethylaminomethylphenol.

5. The method of claim 1, wherein the pharmaceutical composition contains 4-(7-iodoquinolin-4-ylamino)-2-methyloctylaminomethylphenol.

6. The method of claim 1, wherein the pharmaceutical composition contains 4-(7-iodoquinolin-4-ylamino)-2-ethyl(2-hydroxyethyl)aminomethylphenol.

7. The method of claim 1, wherein the pharmaceutical composition contains 4-(7-iodoquinolin-4-ylamino)-2-ethylpropylaminomethylphenol.

* * * * *

UNITED STATES PATENT AND TRADEMARK OFFICE
CERTIFICATE OF CORRECTION

PATENT NO. : 11,571,416 B2
APPLICATION NO. : 16/603907
DATED : February 7, 2023
INVENTOR(S) : Robert A. Davey It is certified that error appears in the above-identified patent and that said Letters Patent is hereby corrected as shown below:

On the Title Page

Column 2, Line 11, Item (56) under Other Publications, delete "Componds." and insert --Compounds.--.

Column 2, Line 12, Item (56) under Other Publications, delete "7-lodo-quinolines," and insert --7-Iodo-quinolines,--.

Column 2, Line 24, Item (56) under Other Publications, delete "NO-donr" and insert --NO-donor--.

Column 2, Line 28, Item (56) under Other Publications, delete "Aminoalkylphenois" and insert --Aminoalkylphenols--.

In the Specification

Immediately after the title of the invention, Column 1, please insert --This invention was made with government support under R21 AI115082 awarded by the National Institutes of Health. The government has certain rights in the invention.--.

In Column 2, Line 41, delete "amiodiaquine." and insert --amodiaquine.--.

In Column 3, Lines 21-22, delete "desetheyl-amodiaquine" and insert --desethyl-amodiaquine--.

In Column 4, Line 46, delete "amiodiaquine." and insert --amodiaquine.--.

In Column 6, Line 10 (Approx.), delete "hydroxyalkandioic" and insert --hydroxyalkanoic--.

In Column 6, Lines 21-22 (Approx.), delete "monohydro genphosphate," and insert --monohydrogen phosphate,--.

Signed and Sealed this
Eighteenth Day of June, 2024

Katherine Kelly Vidal
*Director of the United States Patent and Trademark Office*

CERTIFICATE OF CORRECTION (continued)
U.S. Pat. No. 11,571,416 B2

In Column 18, Line 60, delete "OCH3)," and insert --$OCH_3$),--.

In Column 21, Line 65, delete "$C_{20}H_{24}N_3O+[M+H]^+$" and insert --$C_{20}H_{24}N_3O^+$ $[M+H]^+$--.

In Column 23, Lines 9-10 (Approx.), delete "$C_{20}H_{23}$ $ClN_3O^+$" and insert --$C_{20}H_{23}ClN_3O^+$--.

In Column 32, Line 8 (Approx.), delete "n125.3," and insert --125.3,--.

In Column 40, Lines 27-28, delete "amiodiaquine" and insert --amodiaquine--.

In Column 40, Lines 29-30, delete "amiodiaquine" and insert --amodiaquine--.

In Column 40, Line 49, delete "amiodiaquine," and insert --amodiaquine,--.

In Column 41, Line 3, delete "amiodiaquine" and insert --amodiaquine--.

In Column 41, Line 6, delete "amiodiaquine" and insert --amodiaquine--.

In Column 41, Line 11, delete "amiodiaquine." and insert --amodiaquine.--.

In Column 42, Line 17, delete "amiodiaquine." and insert --amodiaquine.--.